(12) United States Patent
Yuan et al.

(10) Patent No.: US 8,409,254 B2
(45) Date of Patent: Apr. 2, 2013

(54) PROSTHESES, TOOLS AND METHODS FOR REPLACEMENT OF NATURAL FACET JOINTS WITH ARTIFICIAL FACET JOINT SURFACES

(75) Inventors: Hansen A. Yuan, Fayetteville, NY (US); David Stinson, Woodinville, WA (US); Lawrence R. Jones, Conifer, CO (US); Mark A. Reiley, Piedmont, CA (US)

(73) Assignee: Gmedelaware 2 LLC, Audubon, PA (US)

( * ) Notice: Subject to any disclaimer, the term of this patent is extended or adjusted under 35 U.S.C. 154(b) by 641 days.

(21) Appl. No.: 12/163,738

(22) Filed: Jun. 27, 2008

(65) Prior Publication Data

US 2008/0275505 A1 Nov. 6, 2008

Related U.S. Application Data

(63) Continuation of application No. 11/276,541, filed on Mar. 3, 2006, now abandoned, which is a continuation of application No. 10/438,294, filed on May 14, 2003, now abandoned.

(51) Int. Cl.
*A61B 17/70* (2006.01)
*A61B 17/88* (2006.01)

(52) U.S. Cl. .................. 606/247; 606/279
(58) Field of Classification Search .... 623/17.11–17.16; 606/246–279
See application file for complete search history.

(56) References Cited

U.S. PATENT DOCUMENTS

| | | | |
|---|---|---|---|
| 1,308,451 A | 7/1919 | Schachat | |
| 2,502,902 A | 4/1950 | Tofflemire | |
| 2,930,133 A | 3/1960 | Thompson | |
| 2,959,861 A | 11/1960 | Stromquist | |
| 3,596,656 A | 8/1971 | Kaute | |
| 3,710,789 A | 1/1973 | Ersek | |
| 3,726,279 A | 4/1973 | Barefoot et al. | |
| 3,867,728 A | 2/1975 | Stubstad et al. | |
| 3,875,595 A | 4/1975 | Froning | |
| 3,941,127 A | 3/1976 | Froning | |
| 4,040,130 A | 8/1977 | Laure | |
| 4,123,848 A | 11/1978 | Emmerich et al. | |
| 4,156,296 A | 5/1979 | Johnson et al. | |
| 4,210,317 A | 7/1980 | Spann et al. | |
| 4,231,121 A | 11/1980 | Lewis | |
| 4,271,836 A | 6/1981 | Bacal et al. | |
| 4,349,921 A | 9/1982 | Kuntz | |
| 4,394,370 A | 7/1983 | Jefferies | |
| 4,472,840 A | 9/1984 | Jefferies | |
| 4,502,161 A | 3/1985 | Wall | |
| 4,554,914 A | 11/1985 | Kapp et al. | |
| 4,611,581 A | 9/1986 | Steffee | |
| 4,633,722 A | 1/1987 | Beardmore et al. | |

(Continued)

FOREIGN PATENT DOCUMENTS

DE 10135771 A1 7/2001
DE 10312755 A1 10/2003

(Continued)

OTHER PUBLICATIONS

Ochoa et al.; U.S. Appl. No. 12/377,546 entitled "Spinal implant," filed Feb. 13, 2009.

(Continued)

*Primary Examiner* — Eduardo C Robert
*Assistant Examiner* — Nicholas Plionis

(57) ABSTRACT

Cephalad and caudal vertebral facet joint prostheses and methods of use are provided. The cephalad prostheses are adapted and configured to be attached to a lamina portion of a vertebra without blocking a pedicle portion of the cephalad vertebra.

7 Claims, 15 Drawing Sheets

U.S. PATENT DOCUMENTS

| | | |
|---|---|---|
| 4,693,722 A | 9/1987 | Wall |
| 4,697,582 A | 10/1987 | William |
| 4,710,075 A | 12/1987 | Davison |
| 4,759,769 A | 7/1988 | Hedman et al. |
| 4,772,287 A | 9/1988 | Ray et al. |
| 4,778,472 A | 10/1988 | Homsy et al. |
| 4,795,469 A | 1/1989 | Oh |
| 4,805,602 A | 2/1989 | Puno et al. |
| 4,863,477 A | 9/1989 | Monson |
| 4,904,260 A | 2/1990 | Ray et al. |
| 4,911,718 A | 3/1990 | Lee et al. |
| 4,917,701 A | 4/1990 | Morgan |
| 4,932,975 A | 6/1990 | Main et al. |
| 4,950,270 A | 8/1990 | Bowman et al. |
| 4,955,916 A | 9/1990 | Carignan et al. |
| 4,957,495 A | 9/1990 | Kluger |
| 4,987,904 A | 1/1991 | Wilson |
| 5,000,165 A | 3/1991 | Watanabe |
| 5,015,255 A | 5/1991 | Kuslich |
| 5,019,081 A | 5/1991 | Watanabe |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,098,434 A | 3/1992 | Serbousek |
| 5,108,399 A | 4/1992 | Eitenmuller et al. |
| 5,129,900 A | 7/1992 | Asher et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,261,910 A | 11/1993 | Warden et al. |
| 5,284,655 A | 2/1994 | Bogdansky et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,312,409 A | 5/1994 | McLaughlin et al. |
| 5,314,429 A | 5/1994 | Goble |
| 5,314,476 A | 5/1994 | Prewett et al. |
| 5,314,486 A | 5/1994 | Zang et al. |
| 5,314,489 A | 5/1994 | Hoffman et al. |
| 5,314,492 A | 5/1994 | Hamilton et al. |
| 5,329,933 A | 7/1994 | Graf |
| 5,334,203 A | 8/1994 | Wagner |
| 5,348,026 A | 9/1994 | Davidson |
| 5,350,380 A | 9/1994 | Goble et al. |
| 5,360,448 A | 11/1994 | Thramann |
| 5,370,697 A | 12/1994 | Baumgartner |
| 5,401,269 A | 3/1995 | Buttner-Janz et al. |
| 5,405,390 A | 4/1995 | O'Leary et al. |
| 5,413,576 A | 5/1995 | Rivard |
| 5,415,659 A | 5/1995 | Lee et al. |
| 5,415,661 A | 5/1995 | Holmes |
| 5,425,773 A | 6/1995 | Boyd et al. |
| 5,437,669 A | 8/1995 | Yuan et al. |
| 5,437,672 A | 8/1995 | Alleyne |
| 5,443,483 A | 8/1995 | Kirsch |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,470,333 A | 11/1995 | Ray |
| 5,474,551 A | 12/1995 | Finn et al. |
| 5,474,555 A | 12/1995 | Puno et al. |
| 5,491,882 A | 2/1996 | Walston et al. |
| 5,496,318 A | 3/1996 | Howland et al. |
| 5,501,684 A | 3/1996 | Schlapfer et al. |
| 5,507,823 A | 4/1996 | Walston et al. |
| 5,510,396 A | 4/1996 | Prewett et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,569,247 A | 10/1996 | Morrison |
| 5,571,189 A | 11/1996 | Kuslich |
| 5,571,191 A * | 11/1996 | Fitz ............................ 623/17.11 |
| 5,575,792 A | 11/1996 | Errico et al. |
| 5,577,995 A | 11/1996 | Walker et al. |
| 5,587,695 A | 12/1996 | Warmerdam |
| 5,599,311 A | 2/1997 | Raulerson |
| 5,603,713 A | 2/1997 | Aust et al. |
| 5,609,641 A | 3/1997 | Johnson et al. |
| 5,643,258 A * | 7/1997 | Robioneck et al. ............. 606/54 |
| 5,643,263 A | 7/1997 | Simonson |
| 5,645,597 A | 7/1997 | Krapiva |
| 5,645,599 A | 7/1997 | Samani |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,391 A | 11/1997 | Boyd |
| 5,683,392 A | 11/1997 | Richelsoph et al. |
| 5,683,464 A | 11/1997 | Wagner et al. |
| 5,683,466 A | 11/1997 | Vitale |
| 5,688,274 A | 11/1997 | Errico et al. |
| 5,690,630 A | 11/1997 | Errico et al. |
| 5,700,268 A | 12/1997 | Bertin |
| 5,702,450 A | 12/1997 | Bisserie |
| 5,704,941 A | 1/1998 | Jacober et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hendriks et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A | 4/1999 | Harrington |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |
| 5,984,926 A | 11/1999 | Jones |
| 6,001,130 A | 12/1999 | Bryan et al. |
| 6,004,353 A | 12/1999 | Masini |
| 6,010,503 A | 1/2000 | Richelsoph et al. |
| 6,014,588 A | 1/2000 | Fitz |
| 6,019,759 A | 2/2000 | Rogozinski |
| 6,019,792 A | 2/2000 | Cauthen |
| 6,022,350 A | 2/2000 | Ganem |
| 6,039,763 A | 3/2000 | Shelokov |
| 6,048,342 A | 4/2000 | Zucherman et al. |
| 6,050,997 A | 4/2000 | Mullane |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,391 A | 6/2000 | Metz-Stavenhagen et al. |
| 6,077,262 A | 6/2000 | Schläpfer et al. |

| | | | | | | |
|---|---|---|---|---|---|---|
| 6,080,157 | A | 6/2000 | Cathro et al. | 7,220,262 B1 | 5/2007 | Hynes |
| 6,086,590 | A | 7/2000 | Margulies et al. | 7,294,127 B2 | 11/2007 | Leung et al. |
| 6,090,111 | A | 7/2000 | Nichols | 7,302,288 B1 | 11/2007 | Schellenberg |
| 6,113,600 | A | 9/2000 | Drummond et al. | 7,309,338 B2 | 12/2007 | Cragg |
| 6,113,637 | A | 9/2000 | Gill et al. | 7,445,635 B2 | 11/2008 | Fallin et al. |
| 6,120,510 | A | 9/2000 | Albrektsson et al. | 7,547,324 B2 | 6/2009 | Cragg et al. |
| 6,132,430 | A | 10/2000 | Wagner | 2001/0012938 A1 | 8/2001 | Zucherman et al. |
| 6,132,462 | A | 10/2000 | Li | 2001/0020170 A1 | 9/2001 | Zucherman et al. |
| 6,132,464 | A | 10/2000 | Martin | 2002/0004683 A1* | 1/2002 | Michelson ............... 623/17.16 |
| 6,132,465 | A | 10/2000 | Ray et al. | 2002/0013585 A1 | 1/2002 | Gournay et al. |
| 6,165,177 | A | 12/2000 | Wilson et al. | 2002/0013588 A1 | 1/2002 | Landry et al. |
| 6,190,388 | B1 | 2/2001 | Michelson et al. | 2002/0029039 A1 | 3/2002 | Zucherman et al. |
| 6,193,724 | B1 | 2/2001 | Chan | 2002/0042613 A1 | 4/2002 | Mata |
| 6,193,758 | B1 | 2/2001 | Huebner | 2002/0052603 A1 | 5/2002 | Nickols et al. |
| 6,200,322 | B1 | 3/2001 | Branch et al. | 2002/0065557 A1* | 5/2002 | Goble et al. ............... 623/17.11 |
| 6,214,012 | B1 | 4/2001 | Karpman et al. | 2002/0068675 A1 | 6/2002 | Teitelbaum et al. |
| 6,224,602 | B1 | 5/2001 | Hayes | 2002/0082601 A1 | 6/2002 | Toyama et al. |
| 6,231,575 | B1 | 5/2001 | Krag | 2002/0120272 A1 | 8/2002 | Yuan et al. |
| 6,248,105 | B1 | 6/2001 | Schläpfer et al. | 2002/0123752 A1 | 9/2002 | Schultheiss et al. |
| 6,280,443 | B1 | 8/2001 | Gu et al. | 2002/0151895 A1* | 10/2002 | Soboleski et al. ............... 606/61 |
| 6,290,703 | B1 | 9/2001 | Ganem | 2003/0004572 A1* | 1/2003 | Goble et al. ............... 623/17.11 |
| 6,293,949 | B1 | 9/2001 | Justis et al. | 2003/0055427 A1 | 3/2003 | Graf |
| 6,302,890 | B1 | 10/2001 | Leone, Jr. | 2003/0069603 A1 | 4/2003 | Little et al. |
| 6,309,391 | B1 | 10/2001 | Crandall et al. | 2003/0125740 A1 | 7/2003 | Khanna |
| 6,312,431 | B1 | 11/2001 | Asfora | 2003/0181914 A1 | 9/2003 | Johnson et al. |
| 6,340,361 | B1 | 1/2002 | Kraus et al. | 2003/0191532 A1 | 10/2003 | Goble et al. |
| 6,340,477 | B1 | 1/2002 | Anderson | 2003/0195631 A1 | 10/2003 | Ferree |
| 6,342,054 | B1 | 1/2002 | Mata | 2003/0204259 A1 | 10/2003 | Goble et al. |
| 6,361,506 | B1 | 3/2002 | Saenger et al. | 2003/0204261 A1 | 10/2003 | Eisermann et al. |
| 6,368,320 | B1 | 4/2002 | Le Couedic et al. | 2003/0233148 A1 | 12/2003 | Ferree |
| 6,419,703 | B1 | 7/2002 | Fallin et al. | 2004/0006391 A1 | 1/2004 | Reiley |
| 6,440,169 | B1 | 8/2002 | Elberg et al. | 2004/0049205 A1 | 3/2004 | Lee et al. |
| 6,443,954 | B1 | 9/2002 | Bramlet et al. | 2004/0049273 A1 | 3/2004 | Reiley |
| 6,451,021 | B1 | 9/2002 | Ralph et al. | 2004/0049274 A1 | 3/2004 | Reiley |
| 6,471,705 | B1 | 10/2002 | Biedermann et al. | 2004/0049275 A1 | 3/2004 | Reiley |
| 6,514,253 | B1 | 2/2003 | Yao | 2004/0049276 A1 | 3/2004 | Reiley |
| 6,520,963 | B1 | 2/2003 | McKinley | 2004/0049277 A1 | 3/2004 | Reiley |
| 6,524,315 | B1 | 2/2003 | Selvitelli et al. | 2004/0049278 A1 | 3/2004 | Reiley |
| 6,540,749 | B2 | 4/2003 | Schäfer et al. | 2004/0049281 A1 | 3/2004 | Reiley |
| 6,547,790 | B2 | 4/2003 | Harkey, III et al. | 2004/0059429 A1 | 3/2004 | Amin et al. |
| 6,554,843 | B1 | 4/2003 | Ou | 2004/0111154 A1 | 6/2004 | Reiley |
| 6,565,565 | B1 | 5/2003 | Yuan et al. | 2004/0116927 A1 | 6/2004 | Graf |
| 6,565,572 | B2 | 5/2003 | Chappius | 2004/0127989 A1 | 7/2004 | Dooris et al. |
| 6,565,605 | B2 | 5/2003 | Goble et al. | 2004/0143264 A1 | 7/2004 | McAfee |
| 6,572,617 | B1 | 6/2003 | Senegas | 2004/0204710 A1 | 10/2004 | Patel et al. |
| 6,579,319 | B2 | 6/2003 | Goble et al. | 2004/0204718 A1 | 10/2004 | Hoffman |
| 6,585,740 | B2 | 7/2003 | Schlapfer et al. | 2004/0230201 A1 | 11/2004 | Yuan et al. |
| 6,585,769 | B1 | 7/2003 | Muhanna et al. | 2004/0230304 A1 | 11/2004 | Yuan et al. |
| 6,607,530 | B1 | 8/2003 | Carl et al. | 2005/0010291 A1 | 1/2005 | Stinson et al. |
| 6,610,091 | B1 | 8/2003 | Reiley | 2005/0015146 A1 | 1/2005 | Louis et al. |
| 6,619,091 | B2 | 9/2003 | Heffe | 2005/0027361 A1 | 2/2005 | Reiley |
| 6,623,485 | B2 | 9/2003 | Doubler et al. | 2005/0043799 A1 | 2/2005 | Reiley |
| 6,626,909 | B2 | 9/2003 | Chin | 2005/0055096 A1 | 3/2005 | Serhan et al. |
| 6,632,226 | B2 | 10/2003 | Chan | 2005/0080486 A1 | 4/2005 | Fallin et al. |
| 6,638,281 | B2 | 10/2003 | Gorek | 2005/0119748 A1 | 6/2005 | Reiley et al. |
| 6,645,214 | B2 | 11/2003 | Brown et al. | 2005/0131406 A1 | 6/2005 | Reiley et al. |
| 6,648,891 | B2 | 11/2003 | Kim | 2005/0137705 A1 | 6/2005 | Reiley |
| 6,669,698 | B1 | 12/2003 | Tromanhauser et al. | 2005/0137706 A1 | 6/2005 | Reiley |
| 6,669,729 | B2 | 12/2003 | Chin | 2005/0143818 A1 | 6/2005 | Yuan et al. |
| 6,712,818 | B1 | 3/2004 | Michelson | 2005/0149190 A1 | 7/2005 | Reiley |
| 6,712,849 | B2 | 3/2004 | Re et al. | 2005/0234552 A1 | 10/2005 | Reiley |
| 6,736,815 | B2 | 5/2004 | Ginn | 2005/0240264 A1 | 10/2005 | Tokish, Jr. et al. |
| 6,749,361 | B2 | 6/2004 | Hermann et al. | 2005/0240265 A1 | 10/2005 | Kuiper et al. |
| 6,761,698 | B2 | 7/2004 | Shibata et al. | 2005/0240266 A1 | 10/2005 | Kuiper et al. |
| 6,761,720 | B1 | 7/2004 | Senegas | 2005/0251256 A1 | 11/2005 | Reiley |
| 6,770,095 | B2 | 8/2004 | Grinberg et al. | 2005/0261770 A1 | 11/2005 | Kuiper et al. |
| 6,783,527 | B2 | 8/2004 | Drewry et al. | 2005/0267579 A1 | 12/2005 | Reiley et al. |
| 6,790,233 | B2 | 9/2004 | Brodke et al. | 2005/0283238 A1 | 12/2005 | Reiley |
| 6,802,844 | B2 | 10/2004 | Ferree | 2006/0009847 A1 | 1/2006 | Reiley |
| 6,811,567 | B2 | 11/2004 | Reiley | 2006/0009848 A1 | 1/2006 | Reiley |
| 6,902,567 | B2 | 6/2005 | Del Medico | 2006/0009849 A1 | 1/2006 | Reiley |
| 6,902,580 | B2 | 6/2005 | Fallin et al. | 2006/0029186 A1 | 2/2006 | De Villiers et al. |
| 6,908,465 | B2 | 6/2005 | von Hoffmann et al. | 2006/0041311 A1 | 2/2006 | McLeer |
| 6,949,123 | B2 | 9/2005 | Reiley | 2006/0052785 A1 | 3/2006 | Augostino et al. |
| 6,974,478 | B2 | 12/2005 | Reiley et al. | 2006/0058791 A1 | 3/2006 | Broman et al. |
| 6,979,299 | B2 | 12/2005 | Peabody et al. | 2006/0079895 A1 | 4/2006 | McLeer |
| 7,011,658 | B2 | 3/2006 | Young | 2006/0085072 A1 | 4/2006 | Funk et al. |
| 7,044,969 | B2 | 5/2006 | Errico et al. | 2006/0085075 A1 | 4/2006 | McLeer |
| 7,051,451 | B2 | 5/2006 | Augostino et al. | 2006/0100707 A1 | 5/2006 | Stinson et al. |

| | | | |
|---|---|---|---|
| 2006/0100709 A1 | 5/2006 | Reiley et al. | |
| 2006/0122703 A1 | 6/2006 | Aebi et al. | |
| 2006/0149375 A1 | 7/2006 | Yuan et al. | |
| 2006/0184180 A1 | 8/2006 | Augostino et al. | |
| 2006/0265070 A1 | 11/2006 | Stinson et al. | |
| 2007/0079517 A1 | 4/2007 | Augostino et al. | |
| 2007/0088358 A1 | 4/2007 | Yuan et al. | |
| 2007/0093833 A1 | 4/2007 | Kuiper et al. | |
| 2007/0168029 A1 | 7/2007 | Yuan et al. | |
| 2007/0233256 A1 | 10/2007 | Ohrt et al. | |
| 2007/0255411 A1 | 11/2007 | Reiley | |
| 2007/0265706 A1 | 11/2007 | Reiley et al. | |
| 2007/0276374 A1 | 11/2007 | Broman et al. | |
| 2007/0282445 A1 | 12/2007 | Reiley | |
| 2008/0015583 A1 | 1/2008 | Reiley | |
| 2008/0015585 A1 | 1/2008 | Berg et al. | |
| 2008/0015696 A1 | 1/2008 | Reiley | |
| 2008/0045954 A1 | 2/2008 | Reiley et al. | |
| 2008/0082171 A1 | 4/2008 | Kuiper et al. | |
| 2008/0086213 A1 | 4/2008 | Reiley | |
| 2008/0091200 A1 | 4/2008 | Kuiper et al. | |
| 2008/0091201 A1 | 4/2008 | Reiley | |
| 2008/0091202 A1 | 4/2008 | Reiley | |
| 2008/0091204 A1 | 4/2008 | Kuiper et al. | |
| 2008/0091205 A1 | 4/2008 | Kuiper et al. | |
| 2008/0091210 A1 | 4/2008 | Reiley | |
| 2008/0091268 A1 | 4/2008 | Reiley | |
| 2008/0097437 A1 | 4/2008 | Reiley | |
| 2008/0097438 A1 | 4/2008 | Reiley | |
| 2008/0097439 A1 | 4/2008 | Reiley | |
| 2008/0097440 A1 | 4/2008 | Reiley et al. | |
| 2008/0097446 A1 | 4/2008 | Reiley et al. | |
| 2008/0097609 A1 | 4/2008 | Reiley | |
| 2008/0097612 A1 | 4/2008 | Reiley | |
| 2008/0097613 A1 | 4/2008 | Reiley et al. | |
| 2008/0103501 A1 | 5/2008 | Ralph et al. | |
| 2008/0119845 A1 | 5/2008 | Stone et al. | |
| 2008/0125814 A1 | 5/2008 | Yuan et al. | |
| 2008/0132951 A1 | 6/2008 | Reiley et al. | |
| 2008/0140121 A1 | 6/2008 | McLeer | |
| 2008/0177308 A1 | 7/2008 | McLeer | |
| 2008/0177309 A1 | 7/2008 | McLeer | |
| 2008/0177310 A1 | 7/2008 | Reiley | |
| 2008/0177332 A1 | 7/2008 | Reiley et al. | |
| 2008/0200953 A1 | 8/2008 | Reiley et al. | |
| 2008/0249568 A1 | 10/2008 | Kuiper et al. | |

FOREIGN PATENT DOCUMENTS

| | | | |
|---|---|---|---|
| EP | | 1103226 | 5/2001 |
| EP | | 1205152 A1 | 5/2002 |
| EP | | 1254639 A1 | 11/2002 |
| FR | | 2726459 | 5/1996 |
| FR | | 2749155 | 12/1997 |
| FR | | 2844180 | 3/2004 |
| IE | | S970323 | 6/1998 |
| JP | | 59010807 A | 1/1984 |
| JP | | 10082605 A | 3/1998 |
| JP | | 10179622 A | 7/1998 |
| WO | WO 95/05783 A1 | | 3/1995 |
| WO | WO 96/00049 A1 | | 1/1996 |
| WO | WO 98/48717 A1 | | 11/1998 |
| WO | WO 98/56301 A1 | | 12/1998 |
| WO | WO 99/05995 A1 | | 2/1999 |
| WO | WO 99/23963 A1 | | 5/1999 |
| WO | WO 99/60957 A1 | | 12/1999 |
| WO | WO 99/65412 A1 | | 12/1999 |
| WO | WO 00/38582 A1 | | 7/2000 |
| WO | WO 00/62684 A1 | | 10/2000 |
| WO | WO 01/06939 A1 | | 2/2001 |
| WO | WO 01/15638 A1 | | 3/2001 |
| WO | WO 01/28442 A1 | | 4/2001 |
| WO | WO 01/30248 A1 | | 5/2001 |
| WO | WO 01/39678 A1 | | 6/2001 |
| WO | WO 01/67972 A2 | | 9/2001 |
| WO | WO 01/97721 A2 | | 12/2001 |
| WO | WO 02/00270 A1 | | 1/2002 |
| WO | WO 02/00275 A1 | | 1/2002 |
| WO | WO 02/02024 A1 | | 1/2002 |
| WO | WO 02/02158 A1 | | 1/2002 |
| WO | WO 02/34150 A2 | | 5/2002 |
| WO | WO 02/43603 A1 | | 6/2002 |
| WO | WO 02/071960 A1 | | 9/2002 |
| WO | WO 02/089712 A1 | | 11/2002 |
| WO | WO 03/020143 A1 | | 3/2003 |
| WO | WO 03/041618 A2 | | 5/2003 |
| WO | WO 03/075805 A1 | | 9/2003 |
| WO | WO 03/101350 A1 | | 12/2003 |
| WO | WO 2004/071358 A1 | | 8/2004 |
| WO | WO 2004/103227 A1 | | 12/2004 |
| WO | WO 2004/103228 A1 | | 12/2004 |
| WO | WO 2005/009301 A1 | | 2/2005 |

OTHER PUBLICATIONS

Hewko, Brian; U.S. Appl. No. 12/377,552 entitled "Spinal implant," filed Feb. 13, 2009.

Kuiper et al; U.S. Appl. No. 11/577,967 entitled "Crossbar Spinal Prosthesis having a Modular Design and Systems for Treating Spinal Pathologies," filed Apr. 25, 2007.

McLeer, Thomas, U.S. Appl. No. 11/934,719 entitled "Polymeric Joint Complex and Methods of Use" filed Nov. 2, 2007.

Quest et al.; U.S. Appl. No. 12/099,068 entitled "Measurement and trialing system and methods for orthopedic device component selection," filed Apr. 7, 2008.

Reiley, Mark; U.S. Appl. No. 12/176,280 entitled "Facet arthroplasty devices and methods," filed Jul. 18, 2008.

Funk et al; U.S. Appl. No. 12/186,461 entitled "Implantable orthopedic device component selection instrument and methods," filed Aug. 5, 2008.

Abraham, D.J. et al. "Indications and Trends in Use in Cervical Spinal Fusions." Orthop Clin North Am. Oct. 1998; 29(4):731-44.

Farfan, H.F. "Effects of Torsion on The Intervertebral Joints." The Canadian Journal of Surgery, Jul. 1969; 12(3):336-41.

Farfan, H.F. et al. "The Relation of Facet Orientation to Intervertebral Disc Failure." The Canadian Journal of Surgery, Apr. 1967; 10(2):179-85.

Farfan, H.F. The Pathological Anatomy of Degenerative Spondylolisthesis. A Cadaver Study. Spine. Sep.-Oct. 1980; 5(5):412-8.

Goh, J.C. et al. "Influence of PLIF cage size on lumbar spine stability." Spine. Jan. 2000, 25(1) Medline abstract (one page).

Head, W.C. "Wagner surface replacement arthroplasty of the hip." Analysis of fourteen failures in forty-one hips. J Bone Joint Surg. Am; Mar. 1981, 63(3), Medline abstract (one page).

Khoo, L.T. et al. "A biomechanical analysis of the effects of lumbar fusion on the adjacent vetebral motion segment." Proceedings of the 2000 Annual Meeting of the North American Spine Society, New Orleans, pp. 127-128.

Kirkaldy-Willis, W.H. et al. "Pathology and Pathogenesis of Lumbar Spondylosis and Stenosis." Spine. Dec. 1978; 3(4):319-28.

Kotani, Y. et al. The effects of spinal fixation and destabilization on the biomechanical and histologic properties of spinal ligaments. An in vivo study. Spine, Mar. 15, 1998, 23(6), Medline abstract (2 pages).

Lemaire, J.P. et al. "Intervertebral disc prosthesis: results and prospects for the year 2000." Clinical Orthopaedics and Related Research. 1997; No. 337, pp. 64-76.

Lombardi, J.S. et al. "Treatment of Degenerative Spondylolisthesis." Spine. 1985; 10(9): 821-7.

McMillin, C. R. et al. Artificial Spinal Discs with up to Five Years Follow-up. 20th Annual Meeting of the Society for Biomaterials (Abstract) 1994; p. 89.

Nagata, H. et al. "The effects of immobilization of long segments of the spine on the adjacent and distal facet force and lumbrosacral motion". Spine, Dec. 1993; 18(16):2471-2479, (9 pages).

Nibu, K. et al. "Multidirectional stabilizing potential of BAK interbody spinal fusion system for anterior surgery." J Spinal Discord, Aug. 1997; 10(4), Medline abstract (one page).

Posner, I. et al. A "Biomechanical Analysis of the Clinical Stability of the Lumbar and Lumbrosacral Spine." Spine. 1982; 7(4): 374-389.

Rosenberg, N.J. "Degenerative Spondylolisthesis. Predisposing Factors." The Journal of Bone and Joint Surgery. 1975; 57-A(4): 467-74.

Szpalski, M., et al. Spine Arthroplasty: A Historical Review. Eur Spine J. 2002; 11(Suppl. 2): S65-S84.

Tsantrizos, A. et al. "Segmental stability and compressive strength of posterior lumbar interbody fusion implants." Spine, Aug. 1, 2000; 25(15), Medline abstract (one page).

UCR Pedicle Screw System from SeaSpine (information available at http://www.seaspine.com/ UCR_Pedicle_Screw_System.html). Accessed Dec. 5, 2005.

Victrex of Lancashire, Great Britain. (information on Victrex available at http://www.matweb.com). Accessed Dec. 5, 2005.

* cited by examiner

Fig. 7E
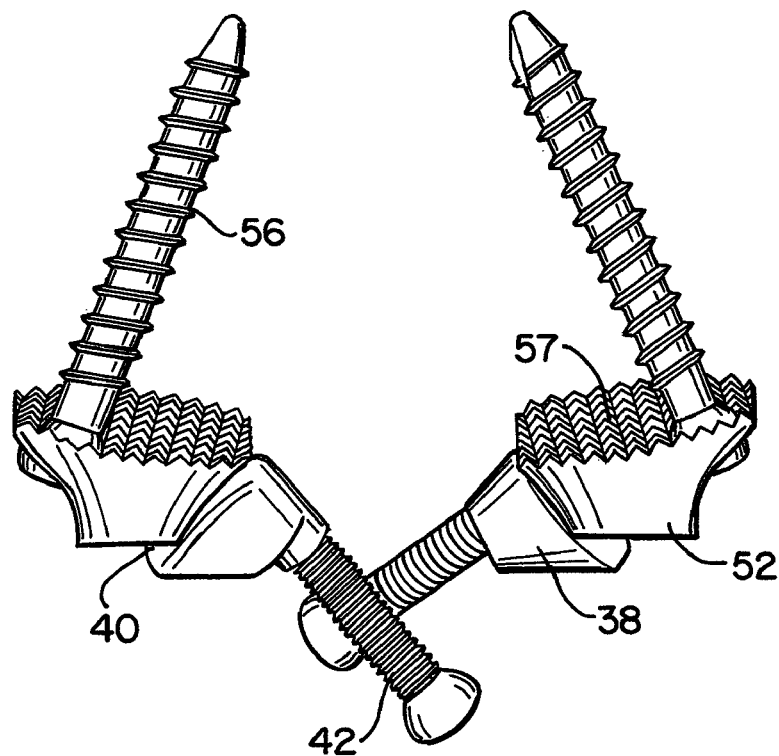
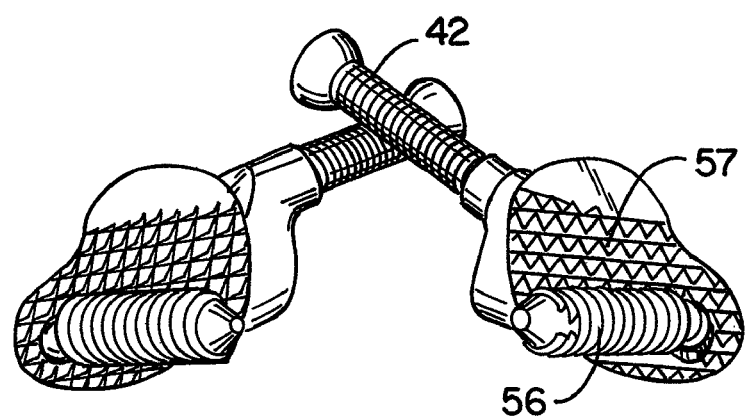
Fig. 7F

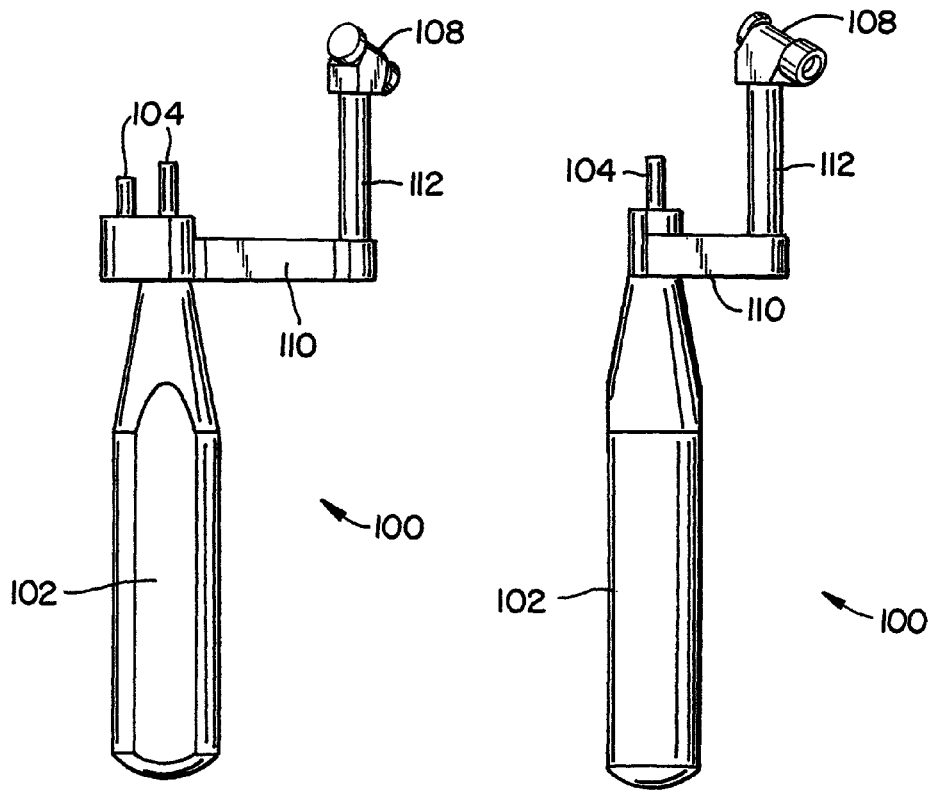
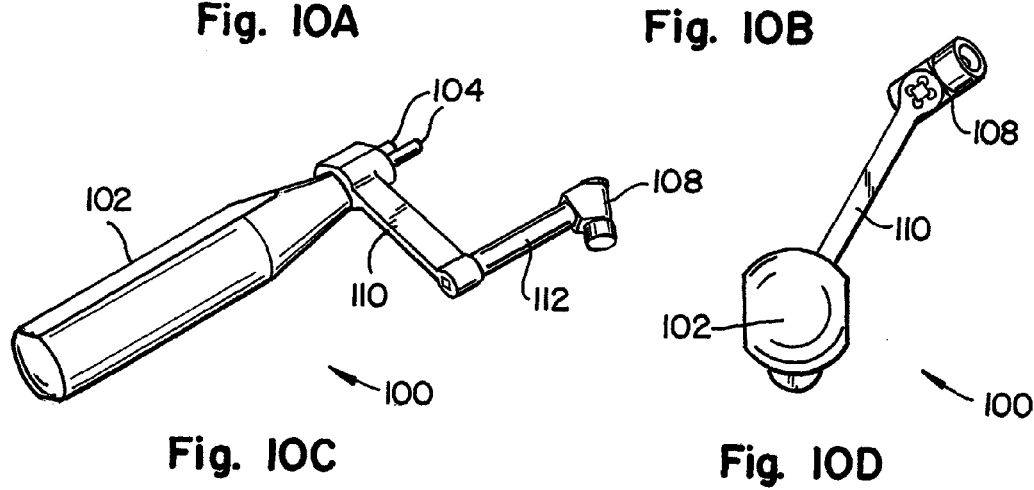
Fig. 10A  Fig. 10B
Fig. 10C  Fig. 10D

US 8,409,254 B2

PROSTHESES, TOOLS AND METHODS FOR REPLACEMENT OF NATURAL FACET JOINTS WITH ARTIFICIAL FACET JOINT SURFACES

CROSS REFERENCE TO RELATED APPLICATIONS

This application is a continuation of pending U.S. application Ser. No. 11/276,541, filed Mar. 3, 2006, entitled "Prostheses, Tools, and Methods for Replacement of Natural Facet Joints with Artificial Facet Joint Surfaces," now abandoned, which is a continuation of U.S. application Ser. No. 10/438,294, filed May 14, 2003, and entitled "prostheses, Tools and Methods for Replacement of Natural Facet Joints with Artificial Facet Joint Surfaces," now abandoned. These applications are incorporated by reference as if fully set forth herein.

FIELD OF THE INVENTION

This invention relates to prostheses for treating various types of spinal pathologies, as well as to methods of treating spinal pathologies.

BACKGROUND OF THE INVENTION

I. Vertebral Anatomy

As FIG. 1 shows, the human spinal column 10 is comprised of a series of thirty-three stacked vertebrae 12 divided into five regions. The cervical region includes seven vertebrae 12, known as C1-C7. The thoracic region includes twelve vertebrae 12, known as T1-T12. The lumbar region contains five vertebrae 12, known as L1-L5. The sacral region is comprised of five vertebrae 12, known as S1-S5. The coccygeal region contains four vertebrae 12, known as Co1-Cu4.

FIG. 2 shows a normal human lumbar vertebra 12. Although the lumbar vertebrae 12 vary somewhat according to location, they share many features common to most vertebrae 12. Each vertebra 12 includes a vertebral body 14 and posterior elements as follows:

Two short bones, the pedicles 16, extend backward from each side of the vertebral body 14 to form a vertebral arch 18. At the posterior end of each pedicle 16 the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 into the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side from the union of the pedicle 16 with the lamina 20. The inferior processes 28 are oval plates of bone that extend in an inferior direction on each side.

The superior and inferior articular processes 26 and 28 each have a natural bony structure known as a facet. The superior articular facet 30 faces upward or superiorly, while the inferior articular facet 31 faces downward. As FIG. 3 shows, when adjacent (i.e., cephalad and caudal) vertebrae 12 are aligned, the facets 30 and 31, capped with a smooth articular cartilage, interlock to form a facet joint 32, also known as a zygapophysial joint.

The facet joint 32 is composed of a superior half and an inferior half. The superior half is formed by the vertebral level below the joint 32, and the inferior half is formed by the vertebral level above the joint 32. For example, in the L4-L5 facet joint, the superior portion of the joint is formed by bony structure on the L-5 vertebra (e.g., a superior articular surface and supporting bone on the L-5 vertebra), and the inferior portion of the joint is formed by bony structure on the L-4 vertebra (e.g., an inferior articular surface and supporting bone on the L-4 vertebra).

As also shown in FIG. 3, an intervertebral disc 34 between each pair of vertebrae 12 permits relative movement between vertebrae 12. Thus, the structure and alignment of the vertebrae 12 permit a range of movement of the vertebrae 12 relative to each other.

II. Facet Joint Dysfunction

Back pain, particularly in the "small of the back", or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebrae can become damaged, such that the vertebrae no longer articulate or properly align with each other. This can result in an undesired anatomy, pain or discomfort, and loss of mobility.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called a "pinched" nerve, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is posterior spinal fusion. Another method of stabilization is anterior spinal fusion, fixation of any number of vertebrae to stabilize and prevent movement of the vertebrae.

Another type of conventional treatment is decompressive laminectomy. This procedure involves excision of the laminae to relieve compression of nerves.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit the relative motion of the vertebrae, altering spine biomechanics.

SUMMARY OF THE INVENTION

There is a need for prostheses, installation tools, and methods that overcome the problems and disadvantages associated with current strategies and designs in various treatments for spine pathologies.

The invention provides prostheses, installation tools, and methods designed to replace natural facet joints at virtually all spinal levels including L1-L2, L2-L3, L3-L4, L4-L5, L5-S1, T-11-T12, and T12-L1. The prostheses, installation tools, and methods can restore a desired anatomy to a spine and give back to an individual a desired range of relative vertebral motion. The prostheses, installation tools, and methods also can lessen or alleviate spinal pain by relieving the source of nerve compression or impingement.

For the sake of description, the prostheses that embody features of the invention will be called either "cephalad" or "caudal" with relation to the portion of a given natural facet joint they replace. As previously described, a given natural facet joint has a superior half and an inferior half. In anatomical terms, the superior half of the joint is formed by the vertebral level below the joint (which can thus be called the caudal portion of the facet joint, i.e., because it is near the feet). The inferior half of the joint is formed by the vertebral level above the joint (which can thus be called the cephalad portion of the facet joint, i.e., because it is near the head). Thus, a prosthesis that, in use, replaces the caudal portion of a facet joint (i.e., the superior half) will be called a "caudal" prosthesis. Likewise, a prosthesis that, in use, replaces the cephalad portion of a facet joint (i.e., the inferior half) will be called a "cephalad" prosthesis.

One aspect of the invention provides a cephalad facet joint prosthesis to replace a cephalad portion of a natural facet joint (e.g., an inferior articular surface and its supporting bone structure on the posterior elements of the vertebra) in the posterior elements of a vertebra. According to this aspect of the invention, the prosthesis includes an artificial facet joint element adapted and configured to replace a cephalad portion of the natural facet joint and a fixation element extending from the artificial facet joint element, the fixation element being adapted and configured to be inserted through a lamina portion of a vertebra to affix the artificial facet joint element to the vertebra, preferably without blocking access to a pedicle portion of the vertebra. The fixation element may also extend through a second lamina portion of the vertebra, such as by traversing the midline of the vertebra through or adjacent to the spinous process. In one embodiment, after installation the cephalad bearing element is disposed between a caudal facet joint bearing surface and a portion of the vertebra, such as a lamina portion.

This aspect of the invention also provides a method of implanting an artificial cephalad facet joint prosthesis on a vertebra and/or the posterior elements of a vertebra. According to this method, a fixation element is inserted through a lamina portion of the vertebra, and a cephalad facet joint bearing surface is placed in a position to form a cephalad portion of a facet joint. An artificial facet joint element is attached to a distal end of the fixation element either after or prior to insertion of the fixation element. The fixation element preferably does not block access to a pedicle portion of the vertebra. The fixation element may also extend through a second lamina portion of the vertebra, such as by traversing the midline of the vertebra through or adjacent to the spinous process. In one embodiment, the placing step includes disposing the artificial facet joint bearing surface between a caudal facet joint bearing surface and a portion of the vertebra, such as a lamina portion. The method may also include the steps of using a guide to define an insertion path for the fixation element and forming a passage through the lamina corresponding to the insertion path.

Another aspect of the invention provides a prosthesis to replace a cephalad portion of a natural facet joint on a vertebra. In this aspect of the invention the prosthesis includes an artificial facet joint element adapted and configured to replace a cephalad portion of the natural facet joint; and a fixation element adapted and configured to affix the artificial facet joint element to the vertebra without blocking access to a pedicle portion of the vertebra. In one embodiment, after installation the cephalad bearing element is disposed between a caudal facet joint bearing surface and a portion of the vertebra, such as a lamina portion.

This aspect of the invention also provides a method for implanting a cephalad facet joint prosthesis to replace a removed cephalad portion of a natural facet joint on a vertebra. The method includes the steps of aligning the cephalad facet joint prosthesis with a caudal facet joint bearing surface; and attaching the cephalad facet joint prosthesis to the vertebra without blocking a pedicle portion of the vertebra. The attaching step of the method may also include disposing the cephalad facet joint prosthesis between the caudal facet joint bearing surface and a portion of the vertebra. The attaching step may also include the step of inserting a fixation element through a portion of the vertebra, such as the lamina. In this case, the method may include the steps of defining an insertion path in the vertebra prior to the inserting step and forming a passage in the vertebra corresponding to the insertion path. A guide may be used to direct the location and orientation of the insertion path.

Another aspect of the invention provides a facet joint prosthesis to replace, on a vertebra, a caudal portion of a natural facet joint (e.g., a superior articular surface and supporting bone structure on the vertebra). The prosthesis includes an artificial facet joint element with a vertebra contacting surface and a caudal bearing surface, the caudal bearing surface being adapted and configured to replace a caudal portion of a natural facet joint and to be substantially entirely posterior of a contact portion of the vertebra when the vertebra contacting surface contacts the contact portion. The prosthesis also includes a fixation element extending from the artificial facet joint element, the fixation element being adapted and configured to be inserted into the vertebra to affix the prosthesis to the vertebra.

Another aspect of the invention provides a prosthesis for replacing a caudal portion and a cephalad portion of a natural facet joint of cephalad and caudal vertebrae of a spine motion segment. The prosthesis includes an artificial cephalad facet joint element adapted and configured to replace a cephalad portion of the natural facet joint, the artificial cephalad facet joint element having a cephalad bearing surface; a cephalad fixation element, the cephalad fixation element being adapted and configured to be inserted through a lamina portion of a vertebra to affix the artificial cephalad facet joint element to the cephalad vertebra; and an artificial caudal facet-joint element adapted and configured to replace a caudal portion of the natural facet joint, the artificial caudal facet joint element including a caudal bearing surface adapted and configured to mate with the cephalad bearing surface.

Yet another aspect of the invention provides a method for implanting a facet joint prosthesis to replace removed cephalad and caudal portions of a natural facet joint of cephalad caudal vertebrae. The method includes the steps of: affixing an artificial caudal facet joint element to the caudal vertebra; inserting a cephalad fixation element through a lamina portion of the cephalad vertebra; and placing an artificial cephalad facet joint bearing surface in a position to form a cephalad portion of a facet joint. The method may also include attaching an artificial cephalad facet joint element comprising the cephalad facet joint bearing surface to an end of the fixation element either prior to or after the inserting step. In one embodiment, the fixation element does not block access to a pedicle portion of the cephalad vertebra. The cephalad fixation element may also extend through a second lamina portion of the cephalad vertebra, such as by traversing the midline of the cephalad vertebra through or adjacent to the spinous process. The placing step may also include the step of disposing the artificial cephalad facet joint bearing surface between the artificial caudal facet joint element and a portion of the cephalad vertebra. An installation fixture may be used to align the caudal and cephalad elements, although the prosthesis may also be installed without using an installation fixture. The method may also include the step of using a guide to define an insertion path for the cephalad fixation element, although the prosthesis may also be installed without using a guide.

Another aspect of the invention provides a prosthesis to replace a caudal portion and a cephalad portion of a natural facet joint of cephalad and caudal vertebrae. The prosthesis may include an artificial cephalad facet joint element adapted and configured to replace a cephalad portion of the natural facet joint, with the artificial cephalad facet joint element including a cephalad bearing surface; a cephalad fixation element adapted and configured to affix the artificial cephalad facet joint element to the cephalad vertebra without blocking access to a pedicle portion of the cephalad vertebra; and an artificial caudal facet joint element adapted and configured to replace a caudal portion of the natural facet joint, the artificial caudal facet joint element including a caudal bearing surface adapted and configured to mate with the cephalad bearing surface. In one embodiment, after installation the cephalad facet joint bearing surface is disposed between a caudal facet joint bearing surface and a portion of the vertebra, such as a lamina portion. In one embodiment, the cephalad bearing surface and the caudal bearing surface each has a width along its respective transverse axis, with the cephalad bearing surface width being shorter than the caudal bearing surface width. The artificial caudal facet joint element may also include a vertebra contacting surface, with the entire caudal bearing surface being adapted configured to be posterior of a contact portion of the caudal vertebra when the vertebra contacting surface contacts the contact portion.

This aspect of the invention also includes a method for implanting a facet joint prosthesis to replace removed cephalad and caudal portions of a natural facet joint of cephalad and caudal vertebrae. The method includes the steps of affixing an artificial caudal facet joint element to the caudal vertebra; and affixing an artificial cephalad facet joint element to the cephalad vertebra in alignment with the artificial caudal facet joint element and without blocking access to a pedicle portion of the cephalad vertebra. The second affixing step may also include the step of disposing the artificial cephalad facet joint element between the artificial caudal facet joint element and a portion of the cephalad vertebra. An installation fixture may be used to align the caudal and cephalad element, although the prosthesis may also be installed without using an installation fixture. The method may also include the step of using a guide to define an insertion path for the cephalad fixation element, although the prosthesis may also be installed without using a guide.

Other features and advantages of the inventions are set forth in the following description and drawings, as well as in the appended claims.

DESCRIPTION OF THE DRAWINGS

FIG. 7E is a bottom view of a pair of artificial cephalad and caudal facet joint prostheses in the embodiment of FIG. 7A;

FIG. 7F is an anterior view of a pair of artificial cephalad and caudal facet joint prostheses in the embodiment of FIG. 7A;

FIGS. 10A-D are views of a guide tool according to one embodiment of the invention;

Figure 1:
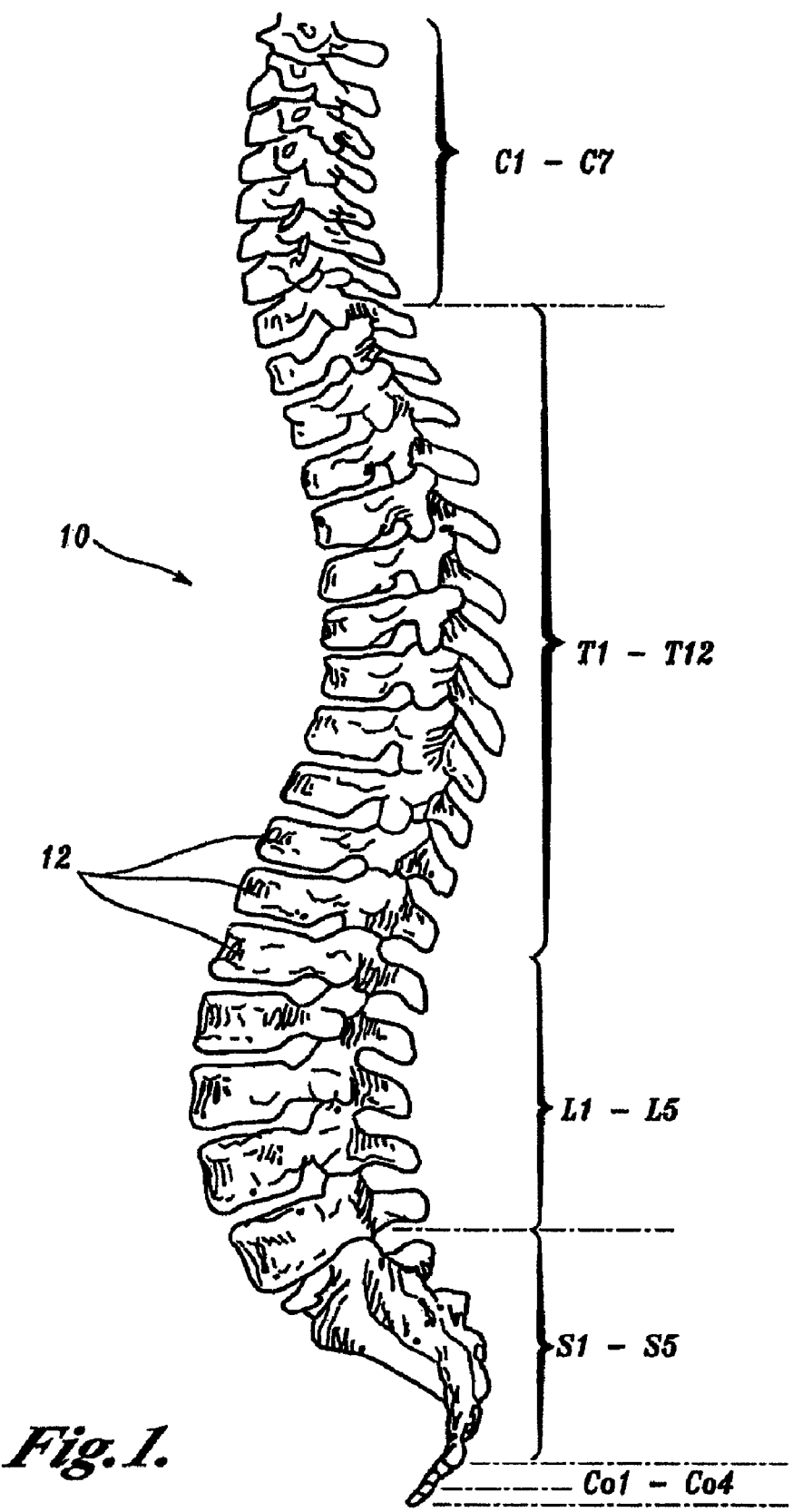
FIG. 1 is a lateral elevation view of a normal human spinal column.
Figure 2:
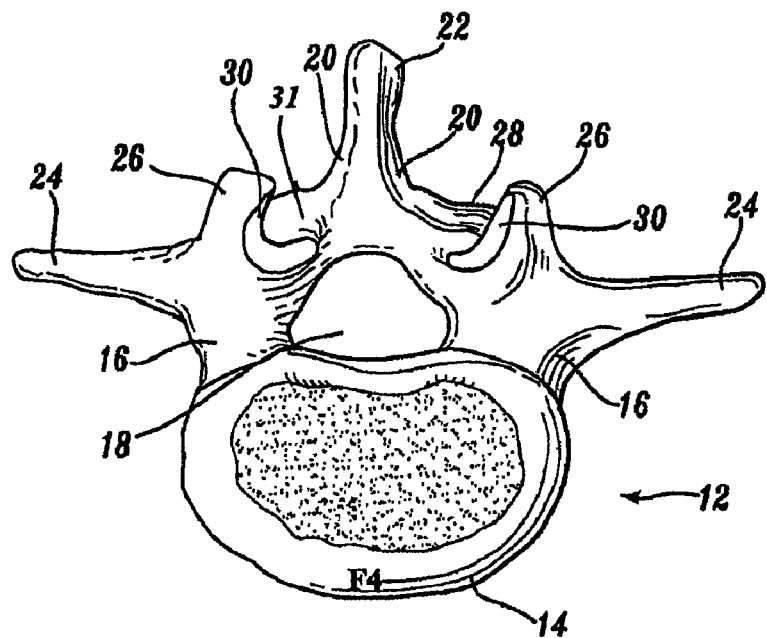
FIG. 2 is a superior view of a normal human lumbar vertebra.
Figure 3:
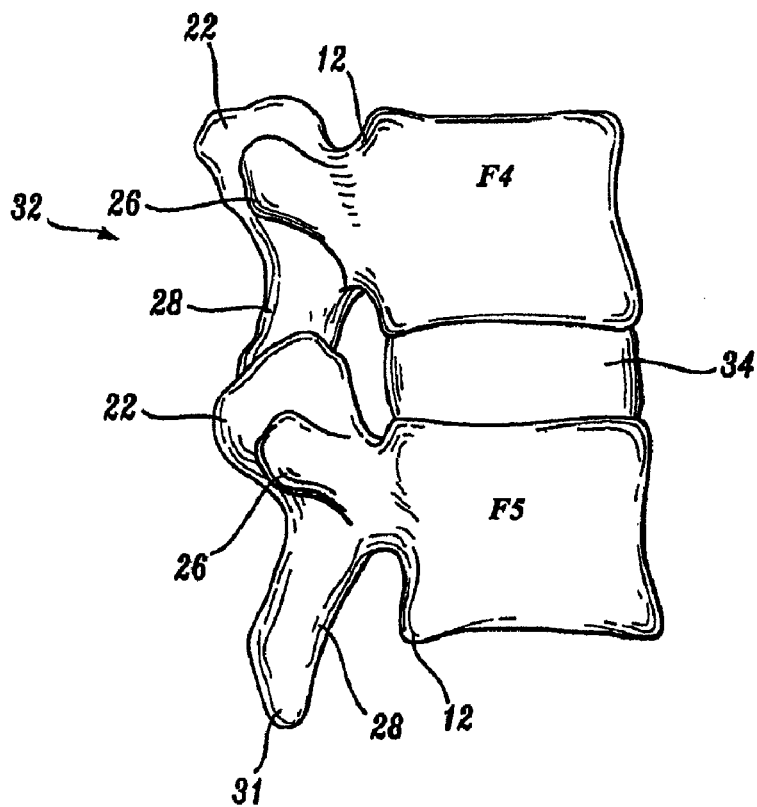
FIG. 3 is a lateral elevation view of a vertebral lumbar facet joint.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

FIGS. 4-7 show artificial cephalad and caudal facet joint prostheses 36 and 50 for replacing a natural facet joint according to one aspect of this invention. Cephalad prosthesis 36 has a bearing element 38 with a bearing surface 40. In this embodiment, bearing surface 40 has a convex shape. Bearing element 38 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts, and bearing surface 40 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Depending on the patient's disease state, the condition of the patient's natural facet joint—including the facet joint's strength, location and orientation—may not be acceptable. As shown in FIGS. 4-7, therefore, the natural cephalad and caudal facet joint surfaces have been removed to enable the installation of a prosthetic facet joint without limitations presented by remaining portions of the natural facet joint.

In one embodiment of the invention, fixation element 42 attaches cephalad prosthesis 36 to a vertebra 60 in an orientation and position that places bearing surface 40 in approximately the same location as the natural facet joint surface the prosthesis replaces. The prosthesis may also be placed in a location other than the natural facet joint location without departing from the invention, such as by orienting the fixation element along a different angle, by moving the joint cephalad or caudad, or by moving the joint medially or laterally.

In the embodiment shown in FIGS. 4-7, fixation element 42 is a screw. Other possible fixation elements include headless screws, stems, corkscrews, wire, staples, adhesives, bone cements, and other materials known in the prosthetic arts.

Figure 4:
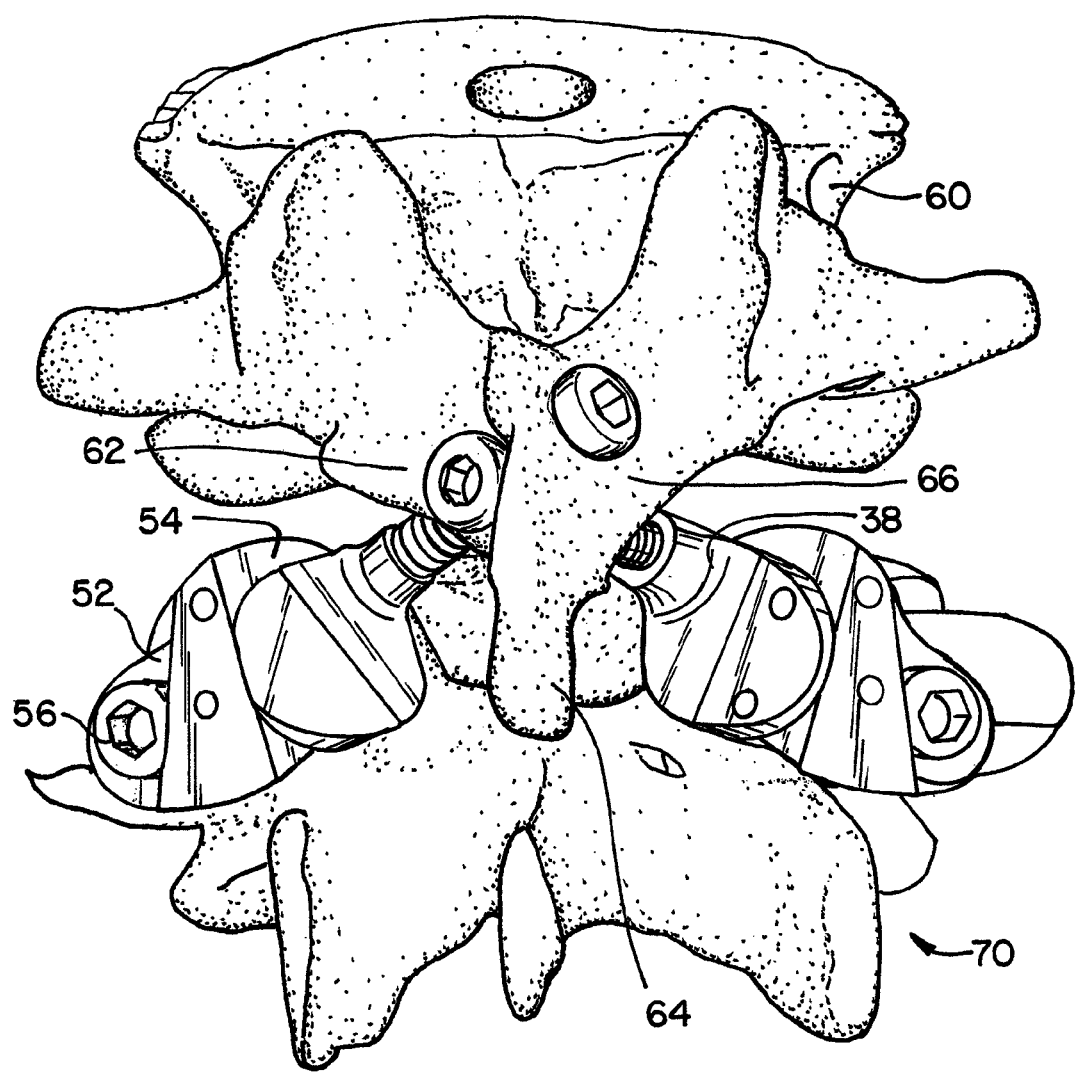
FIG. 4 is a posterior view of an artificial facet joint prosthesis installed in a patient according to one embodiment of this invention.
Figure 5:
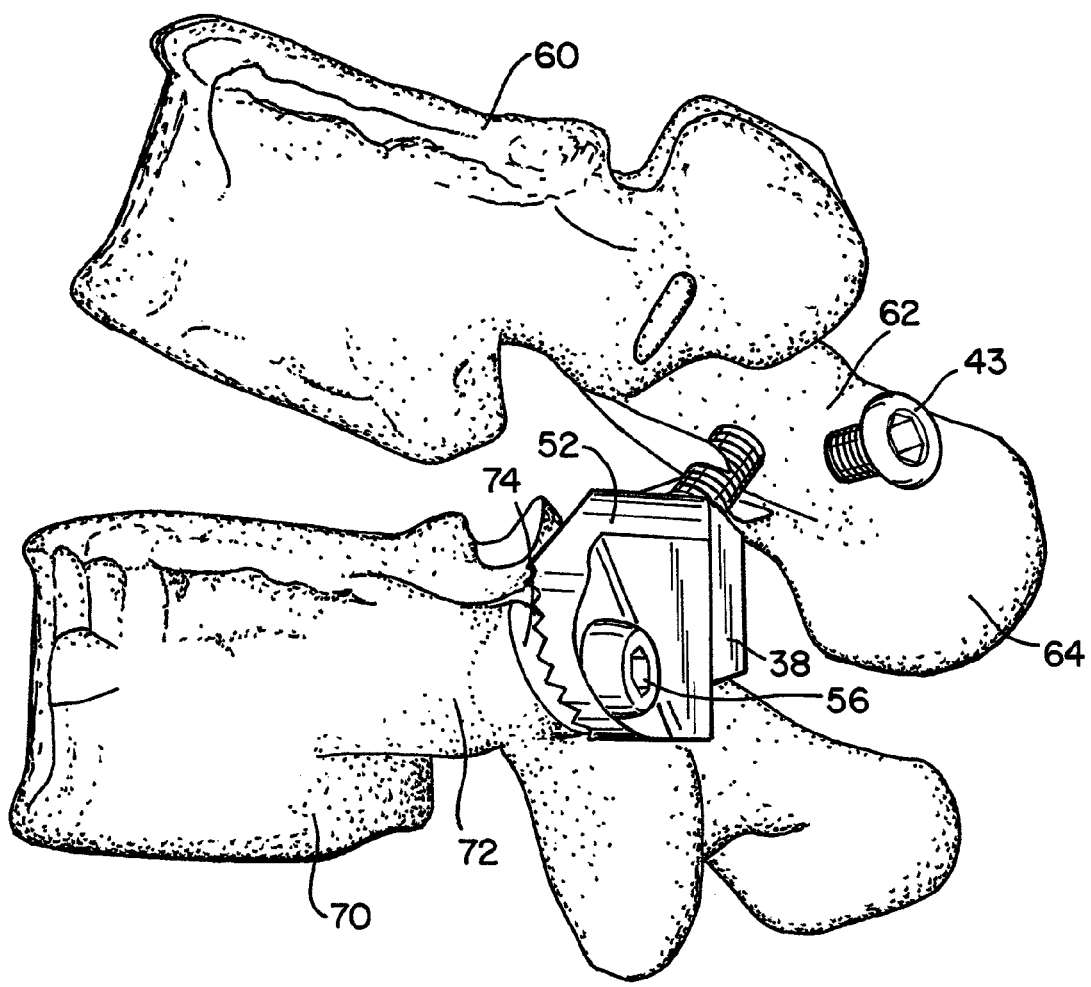
FIG. 5 is a left side view of the embodiment of FIG. 4, as installed in a patient.
Figure 6:
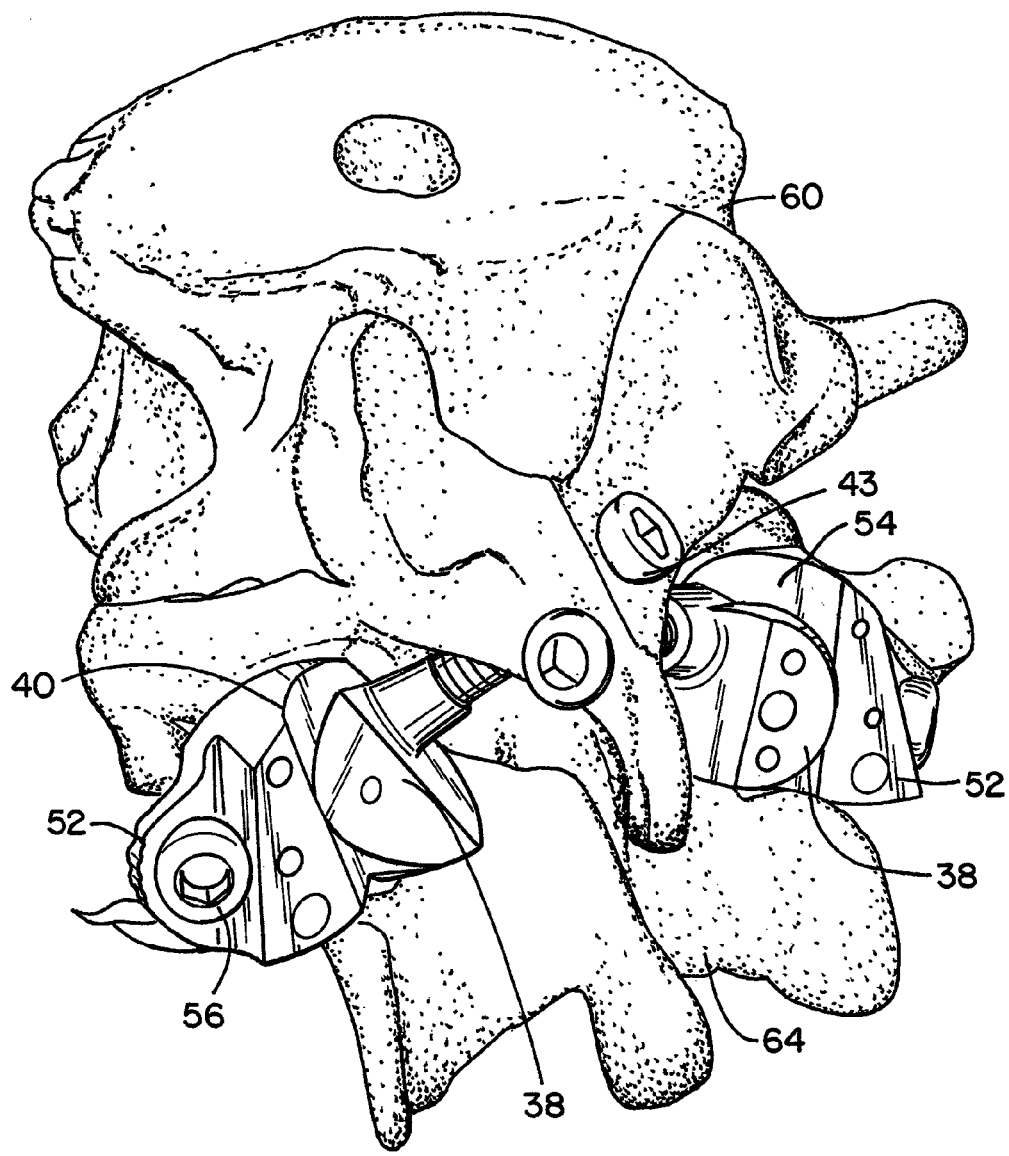
FIG. 6 is yet another view of the embodiment of FIG. 4, as installed in a patient.
Figure 7A:
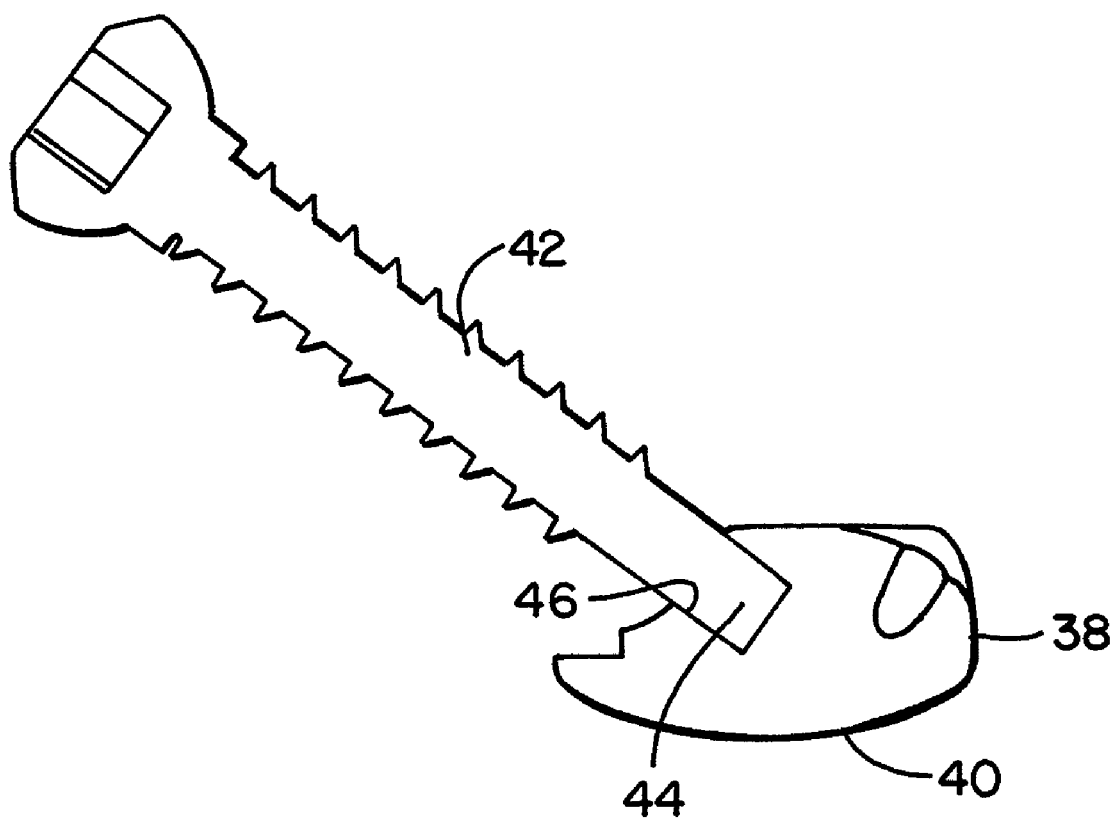
FIG. 7A is a cross-sectional view of a cephalad bearing element and fixation element according to the embodiment of FIG. 4.
Figure 7B:
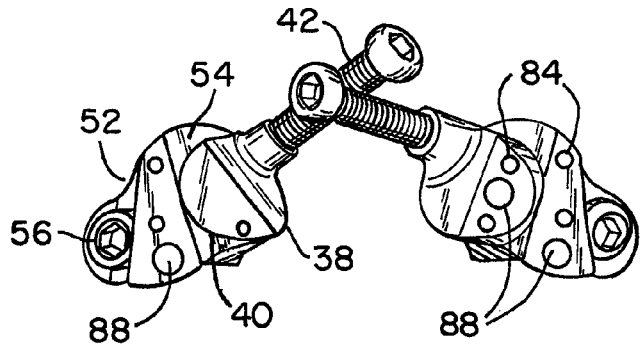
FIG. 7B is a posterior view of a pair of artificial cephalad and caudal facet joint prostheses according to one embodiment of this invention.
Figure 7C:
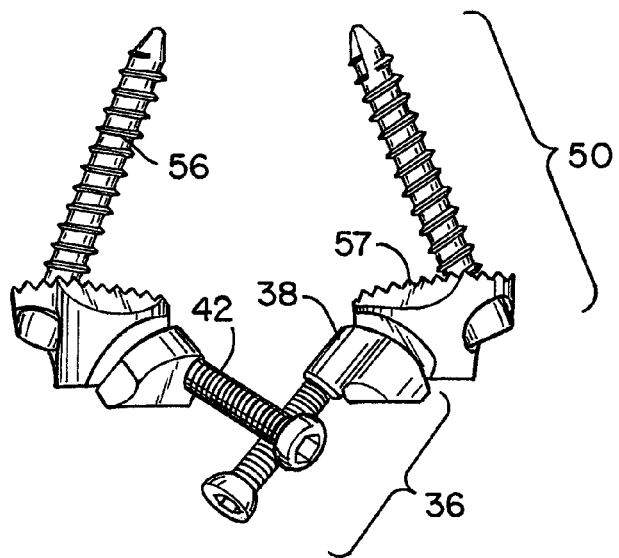
FIG. 7C is a top view of a pair of artificial cephalad and caudal facet joint prostheses in the embodiment of FIG. 7A.
Figure 7D:
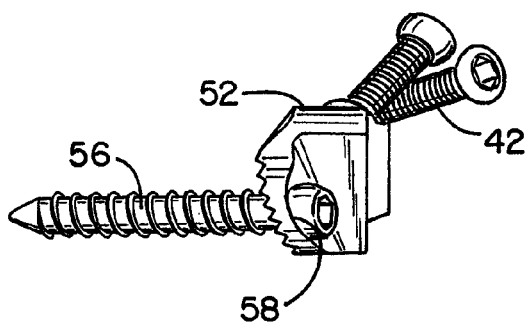
FIG. 7D is a left view of a pair of artificial cephalad and caudal facet joint prostheses in the embodiment of FIG. 7A.
Figure 8A:
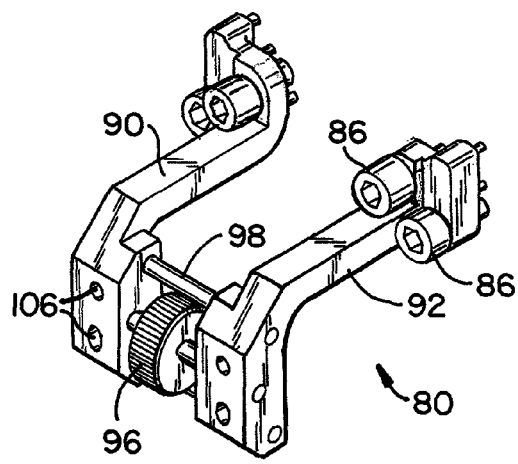
FIG. 8A is a perspective view of an installation fixture according to one embodiment of this invention.
Figure 8B:
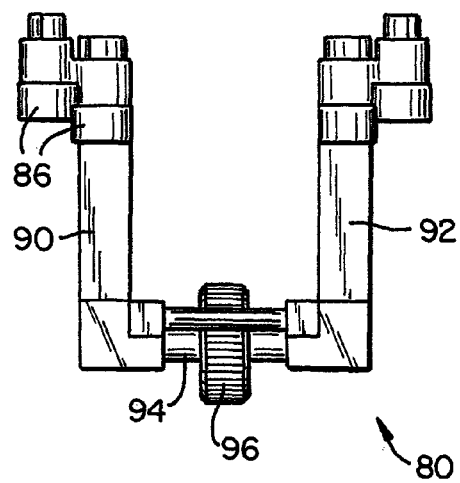
FIG. 8B is a top view of the installation fixture of FIG. 8A.
Figure 8C:
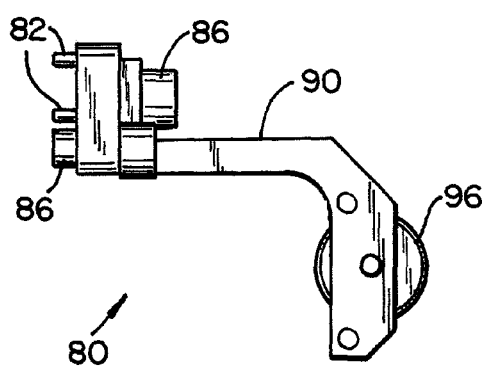
FIG. 8C is a side view of the installation fixture of FIG. 8A.
Figure 8D:
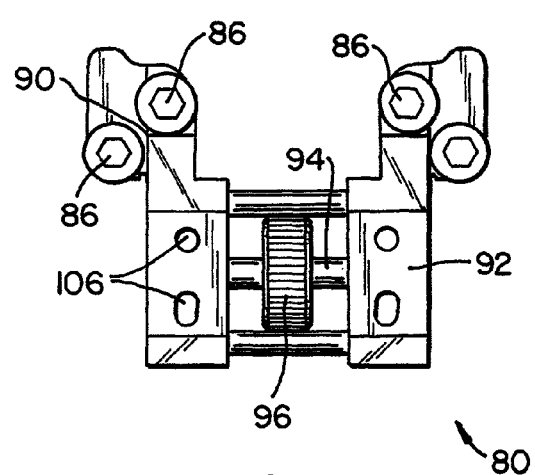
FIG. 8D is a back view of the installation fixture of FIG. 8A.

In this embodiment of the invention, the cephalad facet joint prosthesis attaches to a posterior element of the vertebra, such as one or portions of the lamina and/or the spinous process. For example, as shown in FIGS. 4-6, fixation element 42 may extend through a lamina portion 62 of vertebra 60 at the base of spinous process 64, traversing the vertebra midline as defined by the spinous process 64 and through another lamina portion 66. This orientation of the fixation element is similar to that used in translaminar facet joint screw fixation, as known in the art. Other orientations of fixation element 42 are possible, of course, depending on the dictates of the specific vertebral anatomy and the desires of the clinician. For example, fixation element 42 may extend through only one lamina portion, only through the spinous process, etc.

Unlike other facet joint prostheses that attach to the pedicle, this embodiment's use of one or more posterior elements of the vertebra to attach the cephalad facet joint prosthesis of this invention does not block access to the pedicle area, leaving this area free to be used to attach other prostheses or devices. Other embodiments of the invention may block the pedicle area, of course, without departing from the scope or spirit of the invention. In addition, because of the inherent strength of the lamina, the cephalad facet joint prosthesis may be affixed without the use of bone cement, especially when using a bone ingrowth surface or trabecular metal.

In the orientation shown in FIGS. 4-6 as well as in some alternative embodiments, after insertion the fixation element's proximal end 43 (preferably formed to mate with a suitable insertion tool) and distal end 44 lie on opposite sides of the lamina. Bearing element 38 attaches to the distal end 44 of fixation element 42 to be disposed between a caudal facet joint bearing surface (either natural or artificial, such as the artificial caudal facet joint prosthesis described below) and a portion of the vertebra, such as the lamina portion shown in FIGS. 4-6. To attach bearing element 38 to fixation element 42 in the embodiment shown in FIG. 4, a hole 46 in bearing element 38 is formed with a Morse taper that mates with the distal end 44 of fixation element 42. Other means of attaching bearing element 38 to fixation element 42 may be used, of course, such as other Morse or other taper connections, machine screw threads, NPT screw threads or other known mechanical fastening means. Fixation element 42 may be coated with antimicrobial, antithrombotic, hydroxyapatite, or osteoinductive materials to promote bone ingrowth and fixation. Bearing element 38 may be attached to fixation element 42 before or after implantation in the patient, depending on the manner of implantation and the requirements of the situation.

Prosthesis 36 may be used to form the cephalad portion of a facet joint with either a natural caudal facet joint portion or an artificial caudal facet joint prosthesis.

FIGS. 4-7 also show an artificial caudal joint prosthesis 50 for replacing the superior half of a natural facet joint according to one aspect of this invention. Caudal prosthesis 50 has a bearing element 52 with a bearing surface 54. In this embodiment, bearing surface 54 is concave. Bearing element 52 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts, and bearing surface 54 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

In one embodiment, the natural caudal facet surface has been removed, and fixation element 56 attaches prosthesis 50 to a vertebra 70 via a pedicle in an orientation and position that places bearing surface 54 in approximately the same location as the natural facet joint surface the prosthesis replaces. In an alternative embodiment, the bearing surface 54 may be placed in a location different than the natural facet joint surface, either more medial or more lateral, more cephalad or more caudad, and/or rotated from the natural anatomical orientation and orientation. In addition, in other embodiments the caudal component can be attached to the vertebral body in addition to the pedicle or to the vertebral body alone.

As shown in the embodiment of FIGS. 4-7, fixation element 56 is a screw attached to bearing element 54 via a hole 58 formed in bearing element 52 and is inserted into a pedicle portion 72 of vertebra 70. Other possible fixation elements include stems, corkscrews, wire, staples, adhesives, bone cements, and other materials known in the prosthetic arts. Fixation element 56 can also be inserted into the vertebral body in addition to or in place of the pedicle.

In this embodiment, bearing element 52 has a serrated fixation surface 57 adapted to contact a contact portion 74 of vertebra 70. This optional fixation surface 57 helps prevent rotation of the bearing element 52. In addition, fixation surface 57 may be coated with bone ingrowth material, and any optional serrations increase the surface area for bone ingrowth. As shown in FIG. 5, in this embodiment the entire bearing surface 54 is posterior to surface 57 and contact portion 74.

Prosthesis 50 may be used to form the caudal portion of a facet joint with either a natural cephalad facet joint portion or an artificial cephalad facet joint prosthesis.

FIGS. 7A-F show the artificial facet joint prosthesis according to one embodiment of this invention apart from the vertebrae. As shown, cephalad bearing surface 40 and caudal bearing surface 54 meet to form an artificial facet joint. As seen best in FIG. 7B, the width of caudal bearing surface 54 along its transverse axis is greater than the width of cephalad bearing surface 40 along its transverse axis. This feature helps align the cephalad and caudal joints during implant. In addition, this feature permits the point of contact between the two bearing surface to change with flexion, extension, left and right rotation and lateral bending of the patient's spine.

The prostheses of FIGS. 4-7 may be implanted without special tools. One embodiment of the invention, however, includes an installation fixture to assist with the implantation procedure. FIGS. 8-14 show installation tools used to implant two artificial facet joints, i.e., two cephalad facet joint prostheses and two corresponding caudal facet joint prostheses. The invention also includes installation tools for implanting a single facet joint prosthesis, two caudal facet joint prostheses, two cephalad facet joint prostheses, a caudal and cephalad joint prosthesis, or any other combination of facet joint prostheses.

Figure 9:
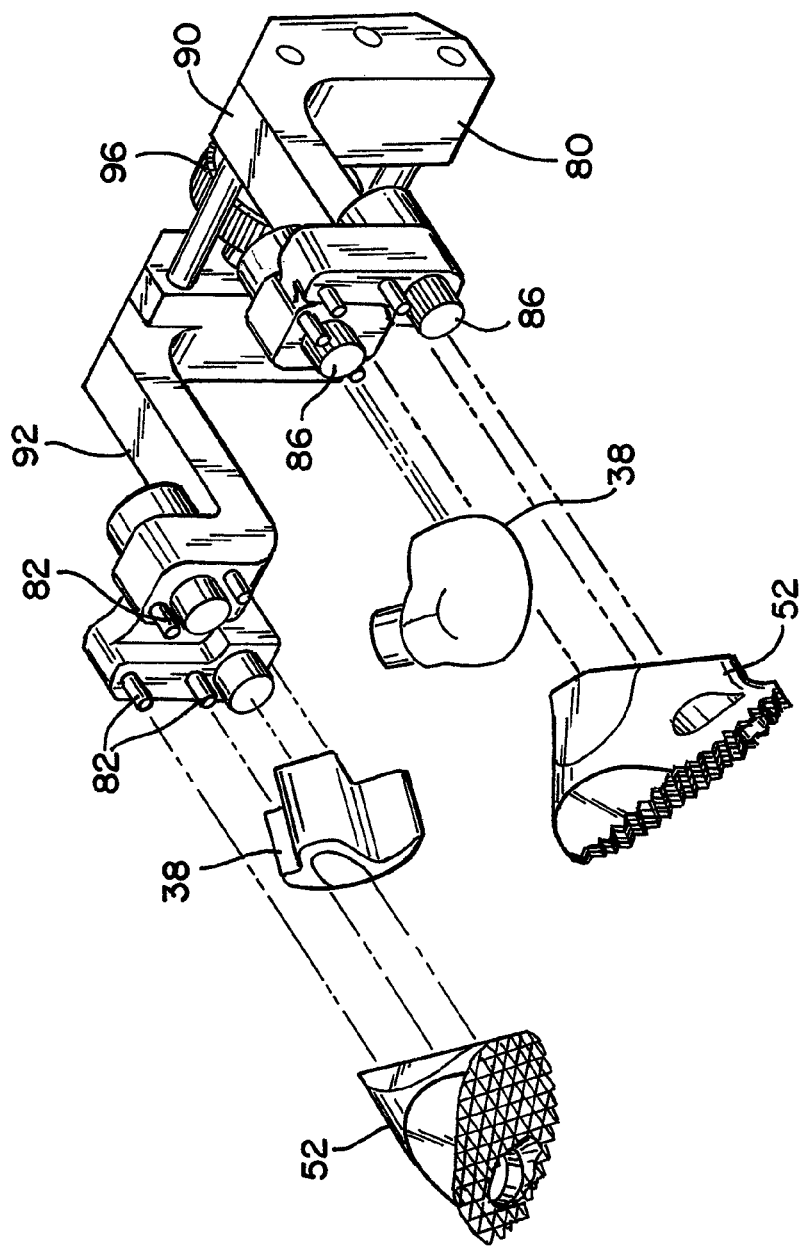
FIG. 9 is an exploded view of the installation fixture of FIG. 8 along with a pair of caudal facet bearing elements and a pair of cephalad facet bearing elements according to one embodiment of the invention.

As shown in FIGS. 8 and 9, installation fixture 80 has alignment elements 82 to align the cephalad bearing elements 38 and caudal bearing elements 52. In this embodiment, the alignment elements are two dowels for each bearing element. Alignment elements 82 mate with corresponding alignment elements in the bearing elements, such as holes 84 (shown, e.g., in FIG. 7B) formed in cephalad bearing elements 38 and caudal bearing elements 52. Other alignment elements may be used, of course, such as pins, grooves, indentations, etc. Attachment elements such as screws 86 attach the bearing elements 38 and 52 to the installation fixture via screw holes 88 (shown, e.g., in FIG. 7B) formed in the bearing elements and in installation fixture 80.

When attached to installation fixture 80, cephalad and caudal bearing surfaces 40 and 54 are in contact and in proper alignment with respect to each other, as shown in FIG. 8. In one embodiment, the cephalad and caudal bearing surfaces 40 and 54 are preloaded to be in compression when attached to installation fixture 80. To bring the pairs of bearing surfaces in proper alignment with respect to the patient's vertebrae, the spacing between the pairs of bearing surfaces might need to be adjusted. In the embodiment of FIGS. 8, 9 and 11-14, installation fixture 80 has two bearing support components 90 and 92 that move in a controlled manner with respect to each other. Specifically, in this embodiment a threaded shaft 94 extends between support components 90 and 92. Shaft 94 engages bores formed in support components 90 and 92; one or both of the bores are threaded so that rotation of shaft 94 causes support components 90 and 92 to move towards or away from each other. Shaft 94 may be provided with a thumbwheel 96 or other actuator for ease of use. One or more guide rods 98 may be provided to maintain the alignment of support components 90 and 92. Other means of moving the cephalad/caudal bearing elements pairs with respect to each other may be used, such as a guided or unguided sliding connection between installation fixture elements.

Figure 11:
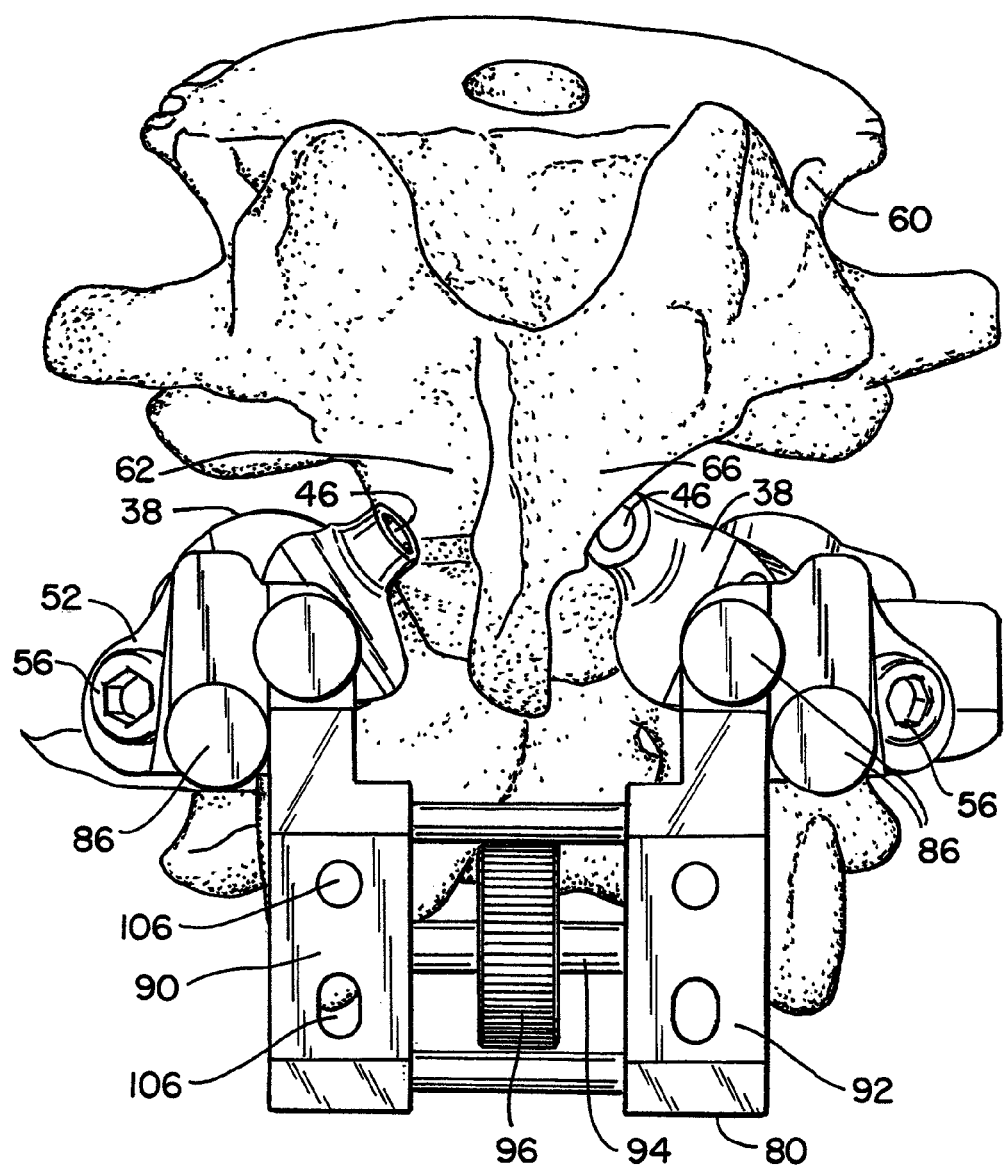
FIG. 11 is a posterior view of the installation fixture of FIGS. 8 and 9 to which a pair of caudal facet bearing elements and a pair of cephalad bearing elements have been attached and with the caudal bearing elements attached to the patient.
Figure 12:
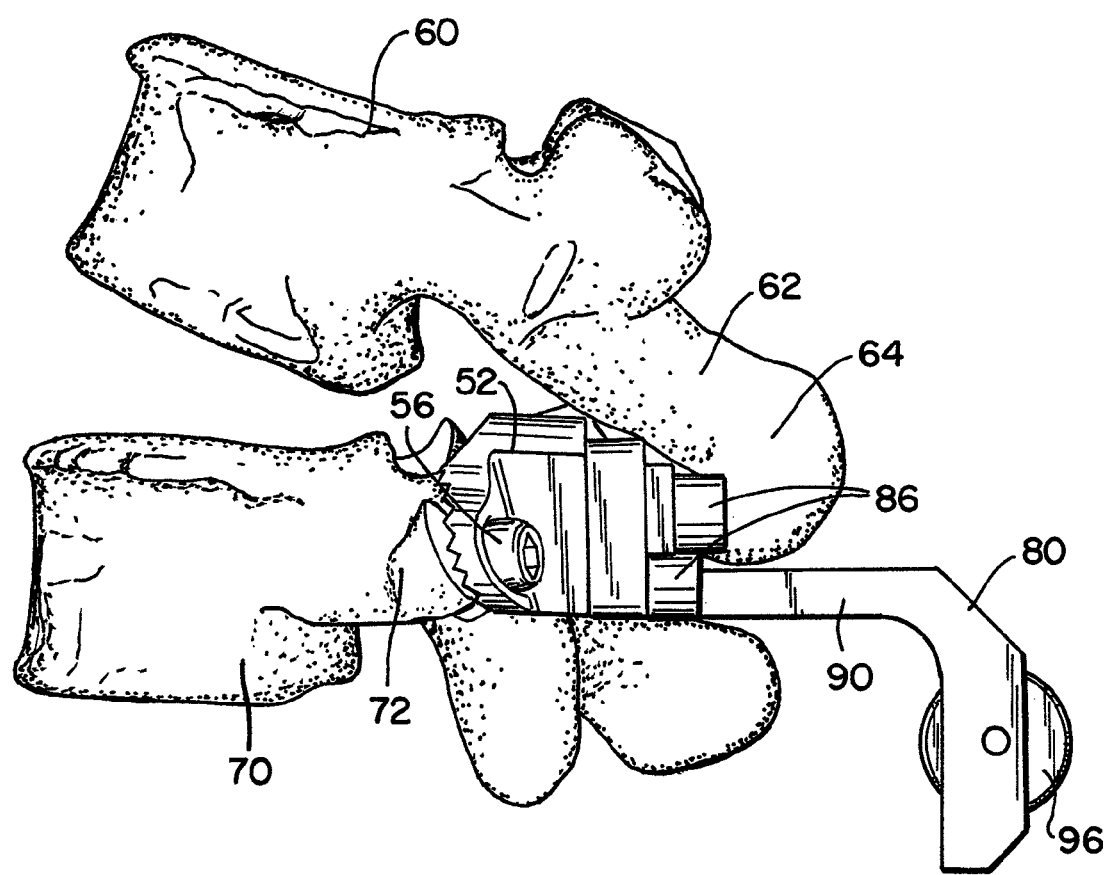
FIG. 12 is a left side view of the installation fixture and bearing elements of FIG. 11 with the caudal bearing elements attached to the patient.

In use, after preparing the implant site by removal of all or a portion of existing natural cephalad and caudal facet joint portions of the cephalad and caudal vertebrae 60 and 70, respectively, of the spine motion segment, bearing elements 38 and 52 are attached to installation fixture 80 as described above. The spacing between the bearing element pairs is then adjusted using thumbwheel 96 to align the fixation holes 58 of caudal bearing elements 52 with the proper fixation screw insertion sites in the pedicle portions of the caudal vertebra (or other suitable location), thus placing the artificial facet joints in positions corresponding to the position of natural facet joints or in any other position desired by the physician, including positions that do not correspond to the position of natural facet joints. Passages aligning with holes 58 are formed and in the pedicle—or into another part of the caudal vertebra near or adjacent to the pedicle—using a drill, awl, pedicle probe, or other tool known in the surgical arts. Fixation screws 56 are then inserted through holes 58 into the pedicle or other portion of the caudal vertebra to attach the caudal bearing elements as well as the entire prosthesis and installation fixture to the caudal vertebra 70, as shown in FIGS. 11 and 12. Alternatively, self-tapping screws or other caudal fixation elements may be used, thereby eliminating the need to pre-fomm the passages.

Thereafter, the cephalad bearing elements are attached to the cephalad vertebra 60. In one embodiment, an insertion path is first determined for each fixation element, then a passage is formed along the insertion path corresponding to cephalad bearing element holes 46 (e.g., in the lamina at the base of the spinous process and through the lamina on the other side, through only one lamina portion, through the spinous process, etc.). Fixation screws 42 can then be inserted through the holes 46 into the passages. Alternatively, self-tapping screws or other caudal fixation elements may be used, thereby eliminating the need to pre-form the passages.

After all four bearing elements have been affixed, the installation fixture 80 may be detached and removed. Installation fixture 80 may be used to implant fewer than four bearing elements, of course.

Figure 13:
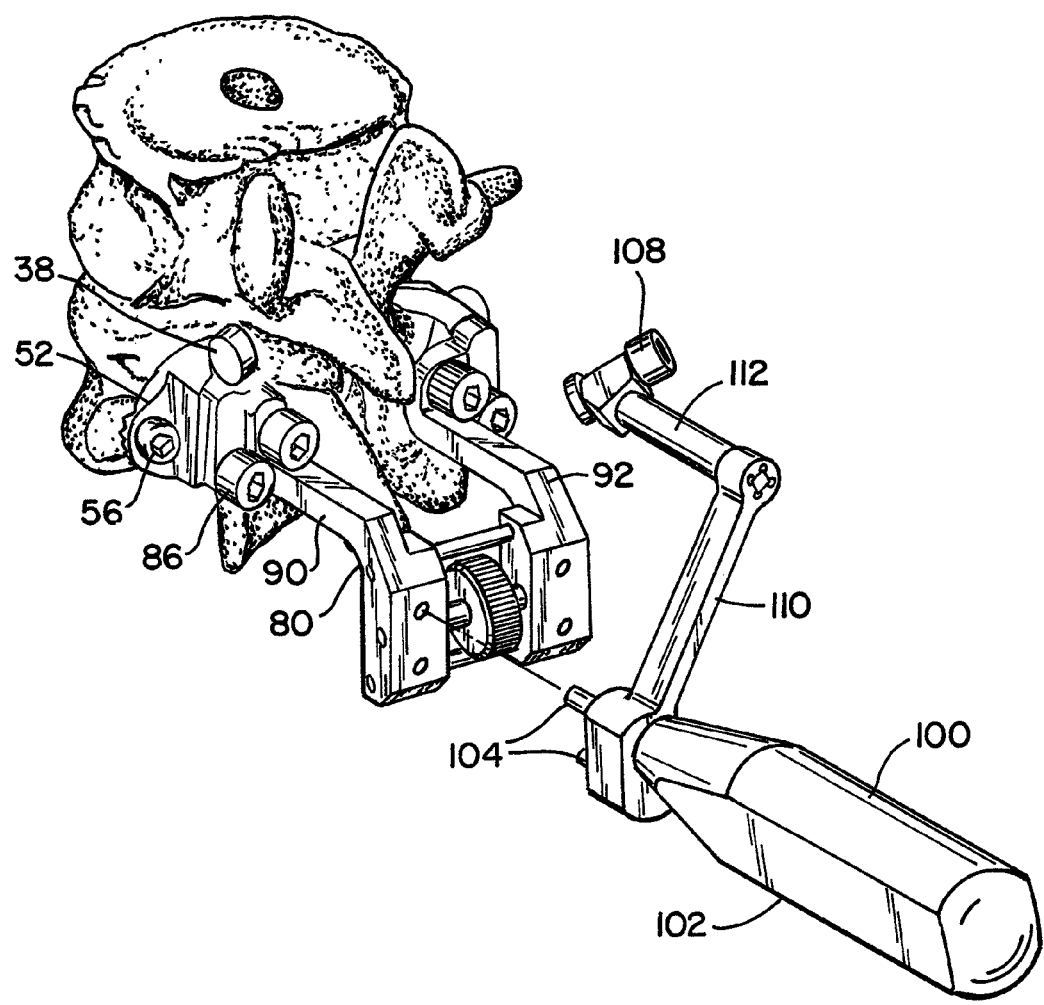
FIG. 13 is a perspective view of the installation fixture and bearing elements of FIGS. 11 and 12 showing a guide tool according to one embodiment of this invention.
Figure 14:
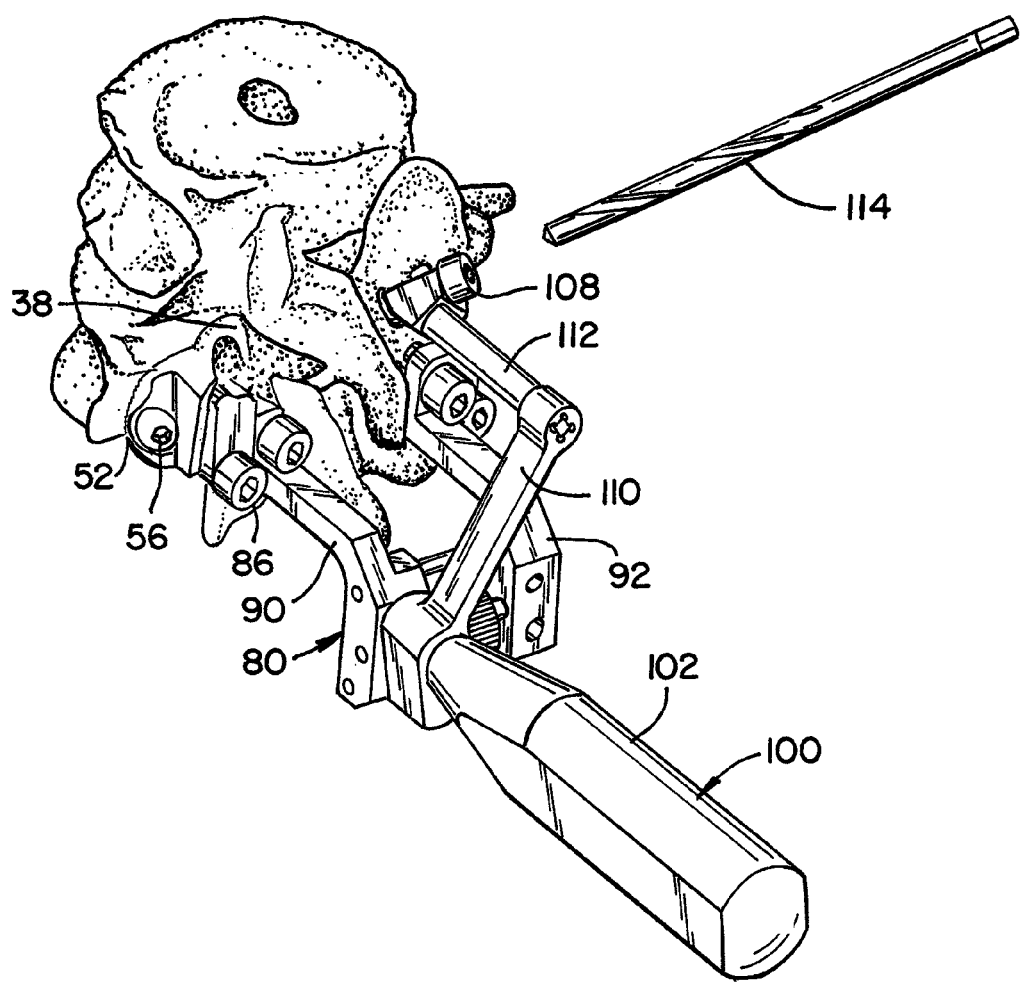
FIG. 14 is a perspective view of the installation fixture and bearing elements of FIGS. 11 and 12 showing the use of a drill bit with the guide tool according to one embodiment of this invention.

FIGS. 10, 13 and 14 show a tool that may be used to define the insertion path (location, orientation, etc.) for the fixation element of the left cephalad bearing element. For example, the tool may be used to guide the formation of a cephalad bearing element attachment passage for the left bearing element. A corresponding mirror image tool may be used for the right cephalad bearing element. In alternative embodiments, a single tool may be used for defining the insertion path for both left and right cephalad bearing elements.

As shown, tool 100 has a handle 102 and an alignment interface (such as dowels 104 in tool 100 and holes 106 in fixture 80) to align the tool in the proper orientation with respect to installation fixture 80 and a cephalad facet joint bearing element. With the caudal and cephalad bearing elements still attached to installation fixture 80 and preferably with caudal bearing elements already affixed to the caudal vertebra 70, tool 100 engages installation fixture through the alignment interface as shown in FIGS. 13 and 14. In this position, tool 100 may be used to define an insertion path for the cephalad fixation elements.

In the embodiment shown in FIGS. 10, 13 and 14, the insertion path guide is a drill guide 108 supported by arms 110 and 112 and is aligned with hole 46 in cephalad bearing element 38 by the alignment interface between installation fixture 80 and guide tool 100. In this embodiment, drill guide 108 is a tube, but other guide elements may be used, such as a guide groove or surface. A drill bit 114 may be inserted through drill guide 108 to form an insertion passage, such as a passage through a lamina portion of the cephalad vertebra. A fixation screw may then be inserted through the passage in the cephalad vertebra and into the Morse taper connection of hole 46 (or other type connection, as discussed above) of cephalad bearing element 38. As discussed above, the fixation screw may be coated with a bone ingrowth material. Alternatively, a self-tapping screw may be used, thereby removing the need to pre-form a passage.

A mirror image tool may then be used to define an insertion path or to form a hole for the right cephalad bearing element, which is then affixed to the vertebral body in the same way. The installation fixture is then removed, such as by unscrewing screws 86.

As mentioned above, in alternative embodiments the guide tool may be used to define a path for a self-tapping screw or other fixation element that does not require the use of a drill. In those embodiments, element 108 may be used to define a path for the self-tapping screw or other fixation element. The fixation element path may be through only a single lamina portion, through the spinous process alone, or any other suitable path.

In some embodiments, the entire prosthesis other than the bearing surface may be coated with bone ingrowth material.

The above described embodiments of this invention are merely descriptive of its principles and are not to be limited. The scope of this invention instead shall be determined from the scope of the following claims, including their equivalents.

What is claimed:

1. A method for providing articulating surfaces for facet joint articular facets comprising:
    installing a prosthesis comprising first and second artificial facet joints located on contralateral sides of a spine, the installation of each artificial facet joint comprising:
        removing at least a portion of a superior articular facet of a first vertebra and an inferior articular face of a second vertebra, the second vertebra immediately above the first vertebra;
        placing an inferior implant having a first fixation element comprising a first screw and having a generally convex articulating surface in a space created by the removed portion of the inferior articular facet of the second vertebra;
        fixing the inferior implant to the second vertebra by extending the first fixation element through a lamina or spinous process of the second vertebra without attachment of the first fixation element to the pedicle of the second vertebra;
        placing a superior implant having a second fixation element comprising a second screw and having a generally curved articulating surface in a space created by the removed portion of the superior articular facet of the first vertebra; and
        fixing the superior implant to the first vertebra by extending the second fixation screw element through a hole formed through a pedicle portion of the first vertebra;
    wherein the articulating surface of the superior implant and the articulating surface of the inferior implant are positioned to articulate with one another following the fixation of the superior implant to the pedicle portion of the first vertebra and the fixation of the inferior implant to the lamina or spinous process of the second vertebra; and
    wherein the steps of placing superior and inferior implants in their respective spaces further comprise:
        attaching the superior implant and inferior implant of the first artificial facet joint to alignment elements of a first bearing support component;
        attaching the superior and inferior implants of the second artificial facet joint to alignment elements of a second bearing support component, the first and second bearing support components extending in a parallel, spaced relationship and being connected to each other at corresponding ends by a threaded shaft; and
        adjusting the spacing between the bearing support components via the threaded shaft to align the first and second artificial facet joints with screw insertion sites of the first and second vertebrae.

2. The method of claim 1, wherein fixing the superior implant further comprises contacting the first vertebra with a serrated fixation surface of the superior implant.

3. The method of claim 1, wherein the alignment elements comprise dowels.

4. The method of claim 1, wherein the alignment elements comprise grooves or indentations.

5. The method of claim 1, further comprising drilling a translaminar hole for the first fixation element.

6. The method of claim 1, wherein the threaded shaft further comprises a thumbwheel.

7. The method of claim 1, wherein at least one of the first and second screws is a self-tapping screw.

* * * * *